US009347063B2

(12) United States Patent
Iversen et al.

(10) Patent No.: US 9,347,063 B2
(45) Date of Patent: May 24, 2016

(54) OLIGONUCLEOTIDE ANALOG AND METHOD FOR TREATING FLAVIVIRUS INFECTIONS

(71) Applicant: Sarepta Therapeutics, Inc., Corvallis, OR (US)

(72) Inventors: Patrick L. Iversen, Corvallis, OR (US); David A. Stein, Corvallis, OR (US)

(73) Assignee: Sarepta Therapeutics, Inc., Corvallis, OR (US)

( * ) Notice: Subject to any disclaimer, the term of this patent is extended or adjusted under 35 U.S.C. 154(b) by 12 days.

(21) Appl. No.: 14/103,603

(22) Filed: Dec. 11, 2013

(65) Prior Publication Data

US 2015/0038462 A1 Feb. 5, 2015

Related U.S. Application Data

(60) Continuation of application No. 12/848,873, filed on Aug. 2, 2010, now Pat. No. 8,618,270, which is a division of application No. 10/913,996, filed on Aug. 5, 2004, now Pat. No. 7,807,801.

(60) Provisional application No. 60/493,043, filed on Aug. 5, 2003, provisional application No. 60/512,003, filed on Oct. 16, 2003.

(51) Int. Cl.
C07H 21/04 (2006.01)
C12N 15/113 (2010.01)

(52) U.S. Cl.
CPC ........ *C12N 15/1131* (2013.01); *C12N 2310/11* (2013.01); *C12N 2310/314* (2013.01); *C12N 2310/3145* (2013.01); *C12N 2310/3233* (2013.01)

(58) Field of Classification Search
None
See application file for complete search history.

(56) References Cited

U.S. PATENT DOCUMENTS

| 7,807,801 B2 | 10/2010 | Iversen et al. |
| 2003/0087851 A1 | 5/2003 | Takaku et al. |

FOREIGN PATENT DOCUMENTS

| WO | 92/03454 A1 | 3/1992 |
| WO | 98/33904 A2 | 8/1998 |
| WO | 00/78341 A1 | 12/2000 |
| WO | 01/92512 A2 | 12/2001 |
| WO | 02/068637 A2 | 9/2002 |
| WO | 02/081495 A1 | 10/2002 |
| WO | 03/033657 A2 | 4/2003 |

OTHER PUBLICATIONS

Abe et al., "Specific inhibition of influenza virus RNA polymerase and nucleoprotein gene expression by liposomally encapsulated antisense phosphorothioate oligonucleotides in MDCK cells," *Antiviral Chemistry and Chemotherapy* 9(3):253-262, 1998.

Agrawal et al., "Site-specific excision from RNA by RNase H and mixed-phosphate-backbone oligodeoxynucleotides," *Proc. Natl. Acad. Sci. USA* 87(4):1401-1405, Feb. 1990.

Anantpadma et al., "Inhibition of Japanese Encephalitis virus replication in cultures cells and mice by a peptide-conjugated morpholino oligomer," *J. Antimicrob. Chemother*, Mar. 18, 2010, 9 pages.

Benimetskaya et al., "Protamine-Fragment Peptides Fused to an SV40 Nuclear Localization Signal Deliver Oligonucleotides That Produce Antisense Effects in Prostate and Bladder Carcinoma Cells," *Bioconjug. Chem.* 13:177-187, 2002.

Blommers et al., "An approach to the structure determination of nucleic acid analogues hybridized to RNA. NMR studies of a duplex between 2'-OMe RNA and an oligonucleotides containing a single amide backbone modification," *Nucleic Acids Research* 22(20):4187-4194, 1994.

Bonham et al., "An assessment of the antisense properties of RNase H-competent and steric-blocking oligomers," *Nucleic Acids Research* 23(7):1197-1203, 1995.

Boudvillain et al., "Transplatin-Modified Oligo(2'-*O*-methyl ribonucleotide)s: A New Tool for Selective Modulation of Gene Expression," *Biochemistry* 36(10):2926-2931, 1997.

Branch, "A good antisense molecule is hard to find," *TIBS* 23:45-50, Feb. 1998.

Brinton, "The Molecular Biology of West Nile Virus: A New Invader of the Western Hemisphere," *Annu. Rev. Microbiol.* 56:371-402, 2002.

Chen et al., "A Concise Method for the Preparation of Peptide and Arginine-Rich Peptide-Conjugated Antisense Oligonucleotide," *Bioconjug. Chem* 14:532-538, 2003.

Corver et al., "Fine Mapping of a *cis*-Acting Sequence Element in Yellow Fever Virus RNA That Is Required for RNA Replication and Cyclization," *Journal of Virology* 77(3):2265-2270, Feb. 2003.

Cross et al., "Solution Structure of an RNA • DNA Hybrid Duplex Containing a 3'-Thioformacetal Linker and a RNA A-Tract," *Biochemistry* 36:4096-4107, 1997.

Dagle et al., "Targeted elimination of zygotic messages in *Xenopus laevis* embryos by modified oligonucleotides possessing terminal cationic linkages," *Nucleic Acids Research* 28(10):2153-2157, 2000.

Deas et al., "Inhibition of Flavivirus Infections by Antisense Oligomers Specifically Suppressing Viral Translation and RNA Replication," *Journal of Virology* 79(8), 2005.

(Continued)

*Primary Examiner* — Michelle S Horning
(74) *Attorney, Agent, or Firm* — Seed IP Law Group PLLC

(57) ABSTRACT

A method of inhibiting replication of a flavivirus in animal cells, and an oligonucleotide compound for use in the method are disclosed. The oligonucleotide analog (i) has a nuclease-resistant backbone, (ii) is capable of uptake by the cells, (iii) contains between 8-40 nucleotide bases, and (iv) has a sequence of at least 8 bases complementary to a region of the virus' positive strand RNA genome that includes at least a portion of SEQ ID NOS:1-4. Exposure of cells infected with a flavivirus to the analog is effective to form within the cells, a heteroduplex structure composed of the virus ssRNA and the oligonucleotide, characterized by a $T_m$ of dissociation of at least 45° C., and having disrupted base pairing between the virus's 5' and 3' cyclization sequences.

30 Claims, 6 Drawing Sheets

(56) References Cited

OTHER PUBLICATIONS

Dias et al., "Antisense Oligonucleotides: Basic Concepts and Mechanisms," *Mol. Cancer Ther.* 1:347-355, Mar. 1, 2002.
Ding et al,. "An oligodeoxyribonucleotide N3'→P5' phosphoramidate duplex forms an A-type helix in solution," *Nucleic Acids Research* 24(2):354-360, 1996.
Database Geneseq Online "WNV DNAzyme Seq ID No. 20601," retrieved from EBI Database Accession No. ACN20585, Abstract, 2004.
Database Geneseq Online "MNV DNAzyme Seq ID No. 21825," retrieved from EBI Database Accession No. ACN21809, Abstract, 2004.
Database Geneseq Online "WNV Minus Strand DNAzyme Seq ID No. 32671," retrieved from EBI Database Accession No. ACN32655, Abstract, 2004.
Database Geneseq Online "WNV Minus Strand DNAzyme Seq ID No. 33989," retrieved from EBI Database Accession No. ACN33973, Abstract, 2004.
Egholm et al., "PNA hybridizes to complementary oligonucleotides obeying the Watson-Crick hydrogen-bonding rules," *Nature* 365:566-568, Oct. 7, 1993.
Enserink, "West Nile's Surprisingly Swift Continental Sweep," *Science* 297(5589):1988-1989, Sep. 20, 2002.
Felgner et al., "Lipofection: A highly efficient, lipid-mediated DNA-transfection procedure," *Proc. Natl. Acad. Sci. USA* 84(21):7413-7417, Nov. 1987.
Gait et al., "Synthetic Analogues of Polynucleotides. Part XII. Synthesis of Thymidine Derivatives containing an Oxyacetamido- or an Oxyformamido-linkage instead of a Phosphodiester Group," *J. Chem. Soc.* [Perkins 1] 0(14):1684-1686, 1974.
Gee et al., "Assessment of High-Affinity Hybridization, RNase H Cleavage, and Covalent Linkage in Translation Arrest by Antisense Oligonucleotides," *Antisense & Nucleic Acid Drug Development* 8(2):103-111, 1998.
Gritsun et al., "Tick-borne encephalitis," *Antiviral Research* 57(1-2):129-146, 2003.
Hahn et al., "Conserved Elements in the 3' Untranslated Region of Flavivirus RNAs and Potential Cyclization Sequences," *J. Mol. Biol.* 198(1):33-41, 1987.
Hayes et al., "Dengue and dengue hemorrhagic fever," *Pediatr. Infect. Dis. J.* 11(4):311-317, 1992.
International Search Report, mailed Apr. 27, 2005, for PCT/US2004/025335, 4 pages.
Jubin et al., "Hepatitis C Virus Internal Ribosome Entry Site (IRES) Stem Loop IIId Contains a Phylogenetically Conserved GGG Triplet Essential for Translation and IRES Folding," *Journal of Virology* 74(22): 10430-10437, Nov. 2000.
Khromykh et al., "Essential Role of Cyclization Sequences in Flavivirus RNA Replication," *Journal of Virology* 75(14):6719-6728, Jul. 2001.
Khromykh et al., "Subgenomic Replicons of the Flavivirus Kunjin: Construction and Applications," *Journal of Virology* 71(2):1497-1505, Feb. 1997.
Lesnikowski et al., "Octa(thymidine methanephosphonates) of partially defined stereochemistry: synthesis and effect of chirality at phosphorus on binding to pentadecadeoxyriboadenylic acid," *Nucleic Acids Research* 18(8):2109-2115, 1990.
Leyssen et al., "Perspectives for the Treatment of Infections with Flaviviridae," *Clinical Microbiology Reviews* 13(1):67-82, Jan. 2000.

Li et al., "Cell Proteins TIA-1 and TIAR Interact with the 3' Stem-Loop of the West Nile Virus Complementary Minus-Strand RNA and Facilitate Virus Replication," *Journal of Virology* 76(23):11989-12000, Dec. 2002.
Men et al., "Dengue Type 4 Virus Mutants Containing Deletions in the 3' Noncoding Region of the RNA Genome: Analysis of Growth Restriction in Cell Culture and Altered Viremia Pattern and Immunogenicity in Rhesus Monkeys," *Journal of Virology* 70(6):3930-3937, Jun. 1996.
Mertes et al., "Synthesis of Carbonate Analogs of Dinucleosides. 3'-Thymidinyl 5'-Thymidinyl Carbonate, 3'-Thymidinyl 5'-(5-Fluoro-2'-deoxyuridinyl) Carbonate, and 3'-(5-Fluoro-2'-deoxyuridinyl)5'-Thymidinyl Carbonate," *J. Med. Chem.* 12(1):154-157, 1969.
Mongkolsapaya et al., "Original antigenic sin and apoptosis in the pathogenesis of dengue hemorrhagic fever," *Nature Medicine* 9(7):921-927, Jul. 2003.
Monia et al., "Nuclease Resistance and Antisense Activity of Modified Oligonucleotides Targeted to Ha-ras," *Journal of Biological Chemistry* 271(24):14533-14540, 1996.
Morrey et al., "Identification of active antiviral compounds against a New York isolate of West Nile virus," *Antiviral Research* 55(1):107-116, 2002.
Moulton et al., "Cellular Uptake of Antisense Morpholino Oligomers Conjugated to Arginine-Rich Peptides," *Bioconjugate Chem.* 15(2):290-299, 2004.
Moulton et al., "HIV Tat Peptide Enhances Cellular Delivery of Antisense Morpholino Oligomers," *Antisense and Nucleic Acid Drug Development* 13:31-43, 2003.
Partridge et al., "A Simple Method for Delivering Morpholino Antisense Oligos into the Cytoplasm of Cells," *Antisense & Nucleic Acid Drug Development* 6(3):169-175, 1996.
Proutski et al., "Secondary structure of the 3' untranslated region of flaviviruses: similarities and differences," *Nucleic Acids Research* 25(6):1194-1202, Mar. 15, 1997.
Raviprakash et al., "Inhibition of dengue virus by novel, modified antisense oligonucleotides," *Journal of Virology* 69(1):69-74, 1995.
Scherret et al., "The Relationships between West Nile and Kunjin Viruses," *Emerging Infectious Diseases* 7(4):697-705, 2001.
Summerton et al., "Morpholino Antisense Oligomers: Design, Preparation, and Properties," *Antisense & Nucleic Acid Drug Development* 7(3):187-195, 1997.
Takegami et al., "Nucleotide sequence at the #' end of Japanese encephalitis virus genomic RNA," *Virology* 152(2):483-486, 1986.
Ternovoi et al., "Tick-Borne Encephalitis with Hemorrhagic Syndrome, Novosibirsk Region, Russia, 1999," *Emerging Infectious Diseases* 9(6):743-746, Jun. 2003.
Toulmé et al., "Targeting RNA structures by antisense oligonucleotides," *Biochimie* 78(7):663-673, 1996.
Wang et al., "Specific Inhibition of Coxsackievirus B3 Translation and Replication by Phosphorothioate Antisense Oligodeoxynucleotides," *Antimicrobial Agents and Chemotherapy* 45(4):1043-4052, Apr. 2001.
You et al., "A Novel in Vitro Replication System for Dengue Virus," *The Journal of Biological Chemistry* 274(47):33714-33722, Nov. 19, 1999.
You et al., "In Vitro RNA Synthesis from Exogenous Dengue Viral RNA Templates Requires Long Range Interactions between 5'- and 3'-Terminal Regions That Influence RNA Structure," *Journal of Biological Chemistry* 276(19):15581-15591, May 2001.
Zeng et al., "Identification of Specific Nucleotide Sequences within the Conserved 3'-SL in the Dengue Type 2 Virus Genome Required for Replication," *Journal of Virology* 72(9):7510-7522, Sep. 1998.

SEQUENCE LISTING

<160> NUMBER OF SEQ ID NOS: 31

<210> SEQ ID NO 1
<211> LENGTH: 8
<212> TYPE: RNA
<213> ORGANISM: Dengue Virus

<400> SEQUENCE: 1 ucaauaug                                                            8

<210> SEQ ID NO 2
<211> LENGTH: 11
<212> TYPE: RNA
<213> ORGANISM: Tick-borne encephalitis virus

<400> SEQUENCE: 2
ggagaacaag a                                                        11

<210> SEQ ID NO 3
<211> LENGTH: 8
<212> TYPE: RNA
<213> ORGANISM: Dengue Virus

<400> SEQUENCE: 3 cauauuga                                                            8

<210> SEQ ID NO 4
<211> LENGTH: 11
<212> TYPE: RNA
<213> ORGANISM: Tick-borne encephalitis virus

<400> SEQUENCE: 4
ucuuguucuc c                                                        11

```
<210> SEQ ID NO 5
<211> LENGTH: 20
<212> TYPE: RNA
<213> ORGANISM: St. Louis encephalitis virus

<400> SEQUENCE: 5
gucaauaugc uaaaacgcgg                                              20

<210> SEQ ID NO 6
<211> LENGTH: 20
<212> TYPE: RNA
<213> ORGANISM: Japanese encephalitis virus

<400> SEQUENCE: 6
aucaauaugc ugaaacgcgg                                              20

<210> SEQ ID NO 7
<211> LENGTH: 20
<212> TYPE: RNA
<213> ORGANISM: Yellow fever virus

<400> SEQUENCE: 7
gucaauaugg uacgacgagg                                              20

<210> SEQ ID NO 8
<211> LENGTH: 21
<212> TYPE: RNA
<213> ORGANISM: Dengue virus

<400> SEQUENCE: 8
cuuucaauau gcugaaacgc g                                            21

<210> SEQ ID NO 9
<211> LENGTH: 21
<212> TYPE: RNA
<213> ORGANISM: Dengue virus

<400> SEQUENCE: 9
cuaucaauau gcugaaacgc g                                            21

<210> SEQ ID NO 10
<211> LENGTH: 22
<212> TYPE: RNA
<213> ORGANISM: Tick-borne encephalitis virus

<400> SEQUENCE: 10
cagcuuagga gaacaagagc ug                                           22

<210> SEQ ID NO 11
<211> LENGTH: 20
<212> TYPE: RNA
<213> ORGANISM: West nile virus

<400> SEQUENCE: 11
ggcugucaau augcuaaaac                                              20

<210> SEQ ID NO 12
<211> LENGTH: 22
<212> TYPE: RNA
<213> ORGANISM: St. Louis encephalitis virus

<400> SEQUENCE: 12
aacagcauau ugacaccugg ga                                           22
```

<210> SEQ ID NO 13
<211> LENGTH: 23
<212> TYPE: RNA
<213> ORGANISM: Yellow fever virus

<400> SEQUENCE: 13
ugggaccaua uugacgccag gga 23

<210> SEQ ID NO 14
<211> LENGTH: 22
<212> TYPE: RNA
<213> ORGANISM: Dengue virus

<400> SEQUENCE: 14
aaacagcaua uugacgcugg ga 22

<210> SEQ ID NO 15
<211> LENGTH: 22
<212> TYPE: RNA
<213> ORGANISM: Tick-borne encephalitis virus

<400> SEQUENCE: 15
cgguucuugu ucucccugag cc 22

<210> SEQ ID NO 16
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 16
ccgcgtttta gcatattgac 20

<210> SEQ ID NO 17
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 17
ccgcgtttca gcatattgat 20

<210> SEQ ID NO 18
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 18
cctcgtcgta ccatattgac 20

<210> SEQ ID NO 19
<211> LENGTH: 21
<212> TYPE: DNA
<213> ORGANISM: Artificial Sequence
<220> FEATURE:
<223> OTHER INFORMATION: Synthetic antisense oligomer

<400> SEQUENCE: 19
cgcgtttcag catattgaaa g 21

```
<210> SEQ ID NO 20
<211> LENGTH: 22
<212> TYPE: DNA
<213> ORGANISM: Artificial Sequence
<220> FEATURE:
<223> OTHER INFORMATION: Synthetic antisense oligomer

<400> SEQUENCE: 20
cagctcttgt tctcctaagc tg                                              22

<210> SEQ ID NO 21
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 21
gttttagcat attgacagcc                                                 20

<210> SEQ ID NO 22
<211> LENGTH: 22
<212> TYPE: DNA
<213> ORGANISM: Artificial Sequence
<220> FEATURE:
<223> OTHER INFORMATION: Synthetic antisense oligomer

<400> SEQUENCE: 22
tcccaggtgt caatatgctg tt                                              22

<210> SEQ ID NO 23
<211> LENGTH: 23
<212> TYPE: DNA
<213> ORGANISM: Artificial Sequence
<220> FEATURE:
<223> OTHER INFORMATION: Synthetic antisense oligomer

<400> SEQUENCE: 23
tccctggcgt caatatggtc cca                                             23

<210> SEQ ID NO 24
<211> LENGTH: 22
<212> TYPE: DNA
<213> ORGANISM: Artificial Sequence
<220> FEATURE:
<223> OTHER INFORMATION: Synthetic antisense oligomer

<400> SEQUENCE: 24
tcccagcgtc aatatgctgt tt                                              22

<210> SEQ ID NO 25
<211> LENGTH: 22
<212> TYPE: DNA
<213> ORGANISM: Artificial Sequence
<220> FEATURE:
<223> OTHER INFORMATION: Synthetic antisense oligomer

<400> SEQUENCE: 25
ggctcaggga gaacaagaac cg                                              22

<210> SEQ ID NO 26
<211> LENGTH: 22
<212> TYPE: DNA
<213> ORGANISM: Artificial Sequence
<220> FEATURE:
<223> OTHER INFORMATION: Synthetic antisense oligomer
```

```
<400> SEQUENCE: 26
caggtgtcaa tatgctgttt tg                                               22

<210> SEQ ID NO 27
<211> LENGTH: 18
<212> TYPE: DNA
<213> ORGANISM: Artificial Sequence
<220> FEATURE:
<223> OTHER INFORMATION: Synthetic antisense oligomer

<400> SEQUENCE: 27
cccagcgtca atatgctg                                                    18

<210> SEQ ID NO 28
<211> LENGTH: 20
<212> TYPE: RNA
<213> ORGANISM: St. Louis encephalitis virus

<400> SEQUENCE: 28
ccgcguuuua gcauauugac                                                  20

<210> SEQ ID NO 29
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 29
agtctcgact tgctacctca                                                  20

<210> SEQ ID NO 30
<211> LENGTH: 149
<212> TYPE: RNA
<213> ORGANISM: Dengue virus type 2

<400> SEQUENCE: 30
acuuguuagu cuacguggac cgacaaagac agauucuuug agggagcuaa gcucaacgua       60
guucuaacag uuuuuuaauu agagagcaga ucucugauga auaaccaacg aaaaaaggcg      120
agaaguacgc cuuucaauau gcugaaacg                                       149

<210> SEQ ID NO 31
<211> LENGTH: 112
<212> TYPE: RNA
<213> ORGANISM: Dengue virus type 2

<400> SEQUENCE: 31
aaaaaacagc auauugacgc ugggaaagac cagagauccu gcugucuccu cagcaucauu       60
ccaggcacag aacgccagaa aauggaaugg ugcuguugaa ucaacagguu cu              112
```

OLIGONUCLEOTIDE ANALOG AND METHOD FOR TREATING FLAVIVIRUS INFECTIONS

CROSS-REFERENCES TO RELATED APPLICATIONS

This application is a continuation of U.S. application Ser. No. 12/848,873 filed Aug. 2, 2010, now issued as U.S. Pat. No. 8,618,270; which is a divisional of U.S. application Ser. No. 10/913,996 filed Aug. 5, 2004, now issued as (U.S. Pat. No. 7,807,801); which claims priority to U.S. Provisional Application No. 60/493,043 filed Aug. 5, 2003 and U.S. Provisional Application No. 60/512,003 filed Oct. 16, 2003, all of which are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 120178_424C1_SEQUENCE_LISTING. The text file is 5.9 KB, was created on Oct. 20, 2014 and is being submitted electronically via EFS-Web.

FIELD OF THE INVENTION

This invention relates to an oligonucleotide analog for use in treating a flavivirus infection in animals, to an antiviral method employing the analog, and to a method for monitoring binding of the analog to a viral genome target site.

REFERENCES

The following references are related to the background or to methods or protocols that may be employed in the invention.

Agrawal, S., S. H. Mayrand, et al. (1990). "Site-specific excision from RNA by RNase H and mixed-phosphate-backbone oligodeoxynucleotides." *Proc Natl Acad Sci USA* 87(4): 1401-5.

Blommers, M. J., U. Pieles, et al. (1994). "An approach to the structure determination of nucleic acid analogues hybridized to RNA. NMR studies of a duplex between 2'-OMe RNA and an oligonucleotide containing a single amide backbone modification." *Nucleic Acids Res* 22(20): 4187-94.

Bonham, M. A., S. Brown, et al. (1995). "An assessment of the antisense properties of RNase H-competent and steric-blocking oligomers." *Nucleic Acids Res* 23(7): 1197-203.

Boudvillain, M., M. Guerin, et al. (1997). "Transplatin-modified oligo(2'-O-methyl ribonucleotide)s: a new tool for selective modulation of gene expression." *Biochemistry* 36(10): 2925-31.

Brinton, M. A. (2002). "The molecular biology of West Nile Virus: a new invader of the western hemisphere." *Annu Rev Microbiol* 56: 371-402.

Corver, J., E. Lenches, et al. (2003). "Fine mapping of a cis-acting sequence element in yellow fever virus RNA that is required for RNA replication and cyclization." *J Virol* 77(3): 2265-70.

Dagle, J. M., J. L. Littig, et al. (2000). "Targeted elimination of zygotic messages in *Xenopus laevis* embryos by modified oligonucleotides possessing terminal cationic linkages." *Nucleic Acids Res* 28(10): 2153-7.

Ding, D., S. M. Grayaznov, et al. (1996). "An oligodeoxyribonucleotide N3'→P5' phosphoramidate duplex forms an A-type helix in solution." *Nucleic Acids Res* 24(2): 354-60.

Enserink, M. (2002). "INFECTIOUS DISEASE: West Nile's Surprisingly Swift Continental Sweep." *Science* 297(5589): 1988-1989.

Feigner, P. L., T. R. Gadek, et al. (1987). "Lipofection: a highly efficient, lipid-mediated DNA-transfection procedure." *Proc Natl Acad Sci USA* 84(21): 7413-7.

Gait, M. J., A. S. Jones, et al. (1974). "Synthetic-analogues of polynucleotides XII. Synthesis of thymidine derivatives containing an oxyacetamido- or an oxyformamido-linkage instead of a phosphodiester group." *J Chem Soc [Perkin 1]* 0(14): 1684-6.

Gee, J. E., I. Robbins, et al. (1998). "Assessment of high-affinity hybridization, RNase H cleavage, and covalent linkage in translation arrest by antisense oligonucleotides." *Antisense Nucleic Acid Drug Dev* 8(2): 103-11.

Gritsun, T. S., V. A. Lashkevich, et al. (2003). "Tick-borne encephalitis." *Antiviral Res* 57(1-2): 129-46.

Hahn, C. S., Y. S. Hahn, et al. (1987). "Conserved elements in the 3' untranslated region of flavivirus RNAs and potential cyclization sequences." *J Mol Biol* 198(1): 33-41.

Hayes, E. B. and D. J. Gubler (1992). "Dengue and dengue hemorrhagic fever." *Pediatr Infect Dis J* 11(4): 311-7.

Khromykh, A. A., H. Meka, et al. (2001). "Essential role of cyclization sequences in flavivirus RNA replication." *J Virol* 75(14): 6719-28.

Lesnikowski, Z. J., M. Jaworska, et al. (1990). "Octa(thymidine methanephosphonates) of partially defined stereochemistry: synthesis and effect of chirality at phosphorus on binding to pentadecadeoxyriboadenylic acid." *Nucleic Acids Res* 18(8): 2109-15.

Leyssen, P., E. De Clercq, et al. (2000). "Perspectives for the treatment of infections with Flaviviridae." *Clin Microbiol Rev* 13(1): 67-82, table of contents.

Li, W., Y. Li, et al. (2002). "Cell proteins TIA-1 and TIAR interact with the 3' stem-loop of the West Nile virus complementary minus-strand RNA and facilitate virus replication." *J Virol* 76(23): 11989-2000.

Mertes, M. P. and E. A. Coats (1969). "Synthesis of carbonate analogs of dinucleosides. 3'-Thymidinyl 5'-thymidinyl carbonate, 3'-thymidinyl 5'-(5-fluoro-2'-deoxyuridinyl) carbonate, and 3'-(5-fluoro-2'-deoxyuridinyl) 5'-thymidinyl carbonate." *J Med Chem* 12(1): 154-7.

Mongkolsapaya, J., W. Dejnirattisai, et al. (2003). "Original antigenic sin and apoptosis in the pathogenesis of dengue hemorrhagic fever." *Nat Med* 9(7): 921-927.

Morrey, J. D., D. F. Smee, et al. (2002). "Identification of active antiviral compounds against a New York isolate of West Nile virus." *Antiviral Res* 55(1): 107-16.

Moulton, H. M., M. H. Nelson, et al. (2004). "Cellular uptake of antisense morpholino oligomers conjugated to arginine-rich peptides." *Bioconjug Chem* 15(2): 290-9.

Proutski, V., E. A. Gould, et al. (1997). "Secondary structure of the 3' untranslated region of flaviviruses: similarities and differences." *Nucleic Acids Res* 25(6): 1194-202.

Scherret, J. H., M. Poidinger, et al. (2001). "The relationships between West Nile and Kunjin viruses." *Emerg Infect Dis* 7(4): 697-705.

Ternovoi, V. A., G. P. Kurzhukov, et al. (2003). "Tick-borne encephalitis with hemorrhagic syndrome, novosibirsk region, Russia, 1999." *Emerg Infect Dis* 9(6): 743-6.

Toulme, J. J., R. L. Tinevez, et al. (1996). "Targeting RNA structures by antisense oligonucleotides." *Biochimie* 78(7): 663-73.

You, S., B. Falgout, et al. (2001). "In vitro RNA synthesis from exogenous dengue viral RNA templates requires long range interactions between 5'- and 3'-terminal regions that influence RNA structure." *J Biol Chem* 276(19): 15581-91.

Zeng, L., B. Falgout, et al. (1998). "Identification of specific nucleotide sequences within the conserved 3'-SL in the dengue type 2 virus genome required for replication." *J Virol* 72(9): 7510-22.

BACKGROUND OF THE INVENTION

The family Flaviviridae is a group of single, positive-stranded RNA viruses with a genome size from 9-15 kb. They are enveloped viruses of approximately 40-50 nm. Within the Flaviviridae family is the flavivirus genus which includes the prototype yellow fever virus (YFV), the four serotypes of dengue virus (DEN-1, DEN-2, DEN-3, and DEN-4), Japanese encephalitis virus (JEV), Murray Valley encephalitis virus (MVEV), Kunjin virus (KUN), St. Louis encephalitis virus (SLEV), West Nile virus (WNV), Tick-borne encephalitis virus (TBEV), and about 70 other disease causing viruses.

Most flavivirus infections are treated with supportive measures such as anti-pyretics to keep fever down, fluids, antibiotics for secondary bacterial infection, respiratory support as necessary, etc. The use of ribavirin has significant antiviral chemotherapeutic activity against a number of RNA viruses and has been proven to be effective in the treatment of Influenza virus, Respiratory syncytial virus, Lassa fever virus, and Hanta virus infections. Ribavirin in combination with various interferon drugs is used to treat Hepatitis C virus infections. However, the in vitro and in vivo activity of ribavirin against flaviviruses such as dengue and yellow fever is very weak (Leyssen, De Clercq et al. 2000).

Despite four decades of research effort, safe and effective vaccines against most flaviviruses such as dengue are still not available. Although effective vaccines against yellow fever virus and Japanese encephalitis virus exist, these viruses still cause significant disease worldwide. Efforts to develop an effective dengue vaccine are complicated by the epidemiology of the virus. Although immunity to any given dengue serotype induces lifelong immunity for that particular serotype, a second infection with a different serotype can induce dengue hemorrhagic fever and dengue shock syndrome (DHF/DSS), the severe forms of dengue infection with associated mortality over 20% (Mongkolsapaya, Dejnirattisai et al. 2003).

In view of the severity of the diseases associated with flavivirus infection and their pervasiveness in animals and especially man, there is a need for therapeutic compounds and methods for treating a host infected with a flavivirus.

SUMMARY OF THE INVENTION

The invention includes, in one aspect, a method of inhibiting replication of a flavivirus in animal cells, including mammalian and avian cells. In practicing the method, cells are exposed to an oligonucleotide analog (i) having a nuclease-resistant backbone, (ii) capable of uptake by the cells, (iii) containing between 8-40 nucleotide bases, and (iv) having a sequence of at least 8 bases complementary to a region of the virus' positive strand RNA genome that includes at least a portion of one of sequences identified as SEQ ID NOS:1-4, each sequence representing the viral genome's 5' or 3' cyclization sequence in one of two broad class of flaviviruses. In a preferred embodiment, the oligonucleotide analog has a sequence that is complementary to at least a portion of the 3' cyclization sequence of SEQ ID NOS: 3 or 4 in a viral genome's positive strand. Exposure to the compound is effective to form within the cells, a heteroduplex structure composed of the virus ssRNA and the oligonucleotide, characterized by a $T_m$ of dissociation of at least 45° C., and having disrupted base pairing between the virus' 5' and 3' cyclization sequences, as evidenced by inhibition of viral replication in the cells.

In one embodiment, the analog is complementary to all or a portion of one of the sequences of SEQ ID NOS:1-4. In another embodiment, the analog contains a sequence that is capable of forming a heteroduplex structure with a viral sequence that includes of a portion of the genome's 5' cyclization sequence and a complementary portion of the genome's 3' cyclization sequence.

For use in inhibiting replication of any of St. Louis encephalitis virus, Murray Valley encephalitis virus, West Nile virus, Kunjin virus, Japanese encephalitis virus, Yellow fever virus, Dengue virus—Types 1, 2, 3, and 4, or West Nile virus, the oligonucleotide analog to which the cells are exposed has a sequence of at least 8 bases complementary to a region of the virus' positive strand RNA genome that includes at least a portion of SEQ ID NOS:1 or 3, and preferably SEQ ID NO:3. In another embodiment, the oligonucleotide analog contains a sequence capable of forming a heteroduplex structure with a sequence that includes of a portion of the genome's 5' cyclization sequence identified as SEQ ID NO:1 and a complementary portion of the genome's 3' cyclization sequence identified as SEQ ID NO:3.

For use in inhibiting replication of any of Tick borne encephalitis virus, Powassen virus, Louping III virus, Kyasanur Forest disease virus, and Alkhurma virus, the oligonucleotide analog to which the cells are exposed has a sequence of at least 8 bases complementary to a region of the virus' positive strand RNA genome that includes at least a portion of SEQ ID NOS: 2 or 4, and preferably SEQ ID NO:4. In another embodiment, the oligonucleotide analog contains a sequence capable of forming a heteroduplex structure with a sequence that includes a portion of the genome's 5' cyclization sequence identified as SEQ ID NO:2 and a complementary portion of the genome's 3' cyclization sequence identified as SEQ ID NO:4.

A preferred oligonucleotide analog has an uncharged, or substantially uncharged, backbone, such as one of the structures shown in FIGS. 2A-2G, and is preferably composed of 8-25 morpholino subunits linked by a substantially uncharged, phosphorous-containing backbone, such as the structures shown in FIGS. 3A-3D. One preferred analog has the structure shown in FIG. 3B, where X is $NR_2$, where R is H or $CH_3$, and Y and Z are each 0.

For treating a flavivirus infection in an animal subject, including a human subject, the infected cells may be exposed to the oligonucleotide analog by parenteral or oral administration to the infected subject. The method may further include monitoring a body fluid for the appearance of a heteroduplex composed of the oligonucleotide analog and a complementary portion of the viral genome.

In another aspect, the invention includes an oligonucleotide analog for use in inhibiting replication of a flavivirus in animal cells. The analog is characterized by: (i) a nuclease-resistant backbone, (ii) capable of uptake by animal cells, (iii) containing between 8-40 nucleotide bases; (iv) having a sequence of at least 8 bases complementary to a region of the flavivirus's positive strand RNA genome that includes at least a portion of one of the viral genome sequences identified by SEQ ID NOS:1-4, each sequence representing the genome's 5' or 3' cyclization sequence in one of two broad classes of flavivirus, and (v) capable of forming with the flavivirus ssRNA genome, a heteroduplex structure characterized by a $T_m$ of dissociation of at least 45° C., and having disrupted base pairing between the virus' 5' and 3' cyclization sequences, as evidenced by inhibition of viral replication in the cells. The analog has various embodiments, including those described above with respect to the use of the analog in antiviral therapy.

These and other objects and features of the invention will become more fully apparent when the following detailed description of the invention is read in conjunction with the accompanying drawings.

BRIEF DESCRIPTION OF THE DRAWINGS

FIGS. 2A-2G show the backbone structures of various oligonucleotide analogs with uncharged backbones;

FIGS. 4A and 4B are plots of the response of TBEV and WNV to increasing concentrations of TBEV antisense (FIG. 4A) and scrambled-sequence antisense (FIG. 4B)

DETAILED DESCRIPTION OF THE INVENTION

I. Definitions

The terms below, as used herein, have the following meanings, unless indicated otherwise:

The term "oligonucleotide analog" refers to oligonucleotide having (i) a modified backbone structure, e.g., a backbone other than the standard phosphodiester linkage found in natural oligo- and polynucleotides, and (ii) optionally, modified sugar moieties, e.g., morpholino moieties rather than ribose or deoxyribose moieties. The analog supports bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

A substantially uncharged, phosphorus containing backbone in an oligonucleotide analog is one in which a majority of the subunit linkages, e.g., between 60-100%, are uncharged at physiological pH, and contain a single phosphorous atom. The analog contains between 8 and 40 subunits, typically about 8-25 subunits, and preferably about 12 to 25 subunits. The analog may have exact sequence complementarity to the target sequence or near complementarity, as defined below.

A "subunit" of an oligonucleotide analog refers to one nucleotide (or nucleotide analog) unit of the analog. The term may refer to the nucleotide unit with or without the attached intersubunit linkage, although, when referring to a "charged subunit", the charge typically resides within the intersubunit linkage (e.g. a phosphate or phosphorothioate linkage).

A "morpholino oligonucleotide analog" is an oligonucleotide analog composed of morpholino subunit structures of the form shown in FIGS. 3A-3D, where (i) the structures are linked together by phosphorus-containing linkages, one to three atoms long, joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, all of which are incorporated herein by reference.

Figure 3A:
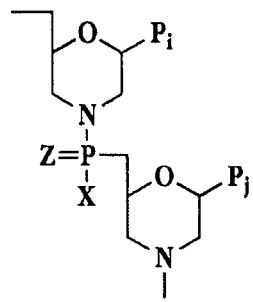
FIGS. 3A-3D show the repeating subunit segment of exemplary morpholino oligonucleotides, designated 3A-3D.
Figure 3B:
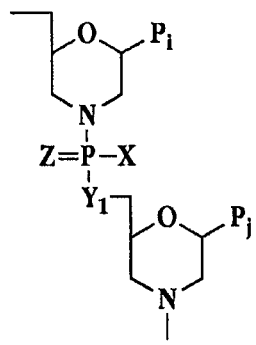

The subunit and linkage shown in FIG. 3B are used for six-atom repeating-unit backbones, as shown in FIG. 3B (where the six atoms include: a morpholino nitrogen, the connected phosphorus atom, the atom (usually oxygen) linking the phosphorus atom to the 5' exocyclic carbon, the 5' exocyclic carbon, and two carbon atoms of the next morpholino ring). In these structures, the atom $Y_1$ linking the 5' exocyclic morpholino carbon to the phosphorus group may be sulfur, nitrogen, carbon or, preferably, oxygen. The X moiety pendant from the phosphorus is any stable group which does not interfere with base-specific hydrogen bonding. Preferred X groups include fluoro, alkyl, alkoxy, thioalkoxy, and alkyl amino, including cyclic amines, all of which can be variously substituted, as long as base-specific bonding is not disrupted. Alkyl, alkoxy and thioalkoxy preferably include 1-6 carbon atoms. Alkyl amino preferably refers to lower alkyl ($C_1$ to $C_6$) substitution, and cyclic amines are preferably 5- to 7-membered nitrogen heterocycles optionally containing 1-2 additional heteroatoms selected from oxygen, nitrogen, and sulfur. Z is sulfur or oxygen, and is preferably oxygen.

A preferred morpholino oligomer is a phosphorodiamidate-linked morpholino oligomer, referred to herein as a PMO. Such oligomers are composed of morpholino subunit structures such as shown in FIG. 3B, where X=$NH_2$, NHR, or $NR_2$ (where R is lower alkyl, preferably methyl), Y=O, and Z=O, and $P_i$ and $P_j$ are purine or pyrimidine base-pairing moieties effective to bind, by base-specific hydrogen bonding, to a base in a polynucleotide. Also preferred are structures having an alternate phosphorodiamidate linkage, where, in FIG. 3B, X=lower alkoxy, such as methoxy or ethoxy, Y=NH or NR, where R is lower alkyl, and Z=O.

The term "substituted", particularly with respect to an alkyl, alkoxy, thioalkoxy, or alkylamino group, refers to replacement of a hydrogen atom on carbon with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic. It may also refer to replacement of a hydrogen atom on a heteroatom (such as an amine hydrogen) with an alkyl, carbonyl or other carbon containing group.

As used herein, the term "target", relative to the viral genomic RNA, refers to a viral genomic RNA, and may include either the positive strand RNA which is the replicative strand of the virus, or the negative or antisense strand which is formed in producing multiple new copies of the positive-strand RNA.

The term "target sequence" refers to a portion of the target RNA against which the oligonucleotide analog is directed, that is, the sequence to which the oligonucleotide analog will hybridize. The target sequence includes at least a portion of one of the sequences identified as SEQ ID NOS:1-4, representing the genome's 5' or 3' cyclization sequences in one of two broad classes of flavivirus, as discussed further below. As will be seen, the target sequence may be a contiguous region of the viral genome, or may be composed of complementary fragments of both the 5' and 3' cyclization sequences of the genome.

The term "targeting sequence" is the sequence in the oligonucleotide analog that is complementary or substantially complementary to the target sequence in the RNA genome. The entire sequence, or only a portion of, the analog may be complementary to the target sequence, or only a portion of the total analog sequence. For example, in an analog having 20 bases, only 8-12 may be targeting sequences. Typically, the targeting sequence is formed of contiguous bases in the analog, but may alternatively be formed of non-contiguous sequences that when placed together, e.g., from opposite ends of the analog, constitute a sequence that spans the target sequence. As will be seen, the target and targeting sequences are selected such that binding of the analog to the viral genome acts to disrupt or prevent formation of RNA secondary structure formed by 5'- and 3'-cyclization sequences in the genome.

Target and targeting sequences are described as "complementary" to one another when hybridization occurs in an antiparallel configuration. A double-stranded polynucleotide can be "complementary" to another polynucleotide. A targeting may have "near" or "substantial" complementarity to the target sequence and still function for the purpose of the present invention. Preferably, the oligonucleotide analogs employed in the present invention have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein.

An oligonucleotide analog "specifically hybridizes" to a target polynucleotide if the oligomer hybridizes to the target under physiological conditions, with a $T_m$ substantially greater than 45° C., preferably at least 50° C., and typically 60° C.-80° C. or higher. Such hybridization preferably corresponds to stringent hybridization conditions. At a given ionic strength and pH, the $T_m$ is the temperature at which 50% of a target sequence hybridizes to a complementary polynucleotide. Again, such hybridization may occur with "near" or "substantial" complementarity of the antisense oligomer to the target sequence, as well as with exact complementarity.

A "nuclease-resistant" oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

A "heteroduplex" refers to a duplex between an oligonucleotide analog and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNAseH, which are capable of cutting double-stranded RNA/RNA or RNA/DNA complexes.

A "base-specific intracellular binding event involving a target RNA" refers to the specific binding of an oligonucleotide analog to a target RNA sequence inside a cell. The base specificity of such binding is sequence specific. For example, a single-stranded polynucleotide can specifically bind to a single-stranded polynucleotide that is complementary in sequence.

An "effective amount" of an antisense oligomer, targeted against an infecting ssRNA virus, is an amount effective to reduce the rate of replication of the infecting virus, and/or viral load, and/or symptoms associated with the viral infection.

As used herein, the term "body fluid" encompasses a variety of sample types obtained from a subject including, urine, saliva, plasma, blood, spinal fluid, or other sample of biological origin, such as skin cells or dermal debris, and may refer to cells or cell fragments suspended therein, or the liquid medium and its solutes.

The term "relative amount" is used where a comparison is made between a test measurement and a control measurement. The relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

"Treatment" of an individual or a cell is any type of intervention provided as a means to alter the natural course of the individual or cell. Treatment includes, but is not limited to, administration of e.g., a pharmaceutical composition, and may be performed either prophylactically, or subsequent to the initiation of a pathologic event or contact with an etiologic agent. The related term "improved therapeutic outcome" relative to a patient diagnosed as infected with a particular virus, refers to a slowing or diminution in the growth of virus, or viral load, or detectable symptoms associated with infection by that particular virus.

An agent is "actively taken up by mammalian cells" when the agent can enter the cell by a mechanism other than passive diffusion across the cell membrane. The agent may be transported, for example, by "active transport", referring to transport of agents across a mammalian cell membrane by e.g. an ATP-dependent transport mechanism, or by "facilitated transport", referring to transport of antisense agents across the cell membrane by a transport mechanism that requires binding of the agent to a transport protein, which then facilitates passage of the bound agent across the membrane. For both active and facilitated transport, the oligonucleotide analog preferably has a substantially uncharged backbone, as defined below. Alternatively, the antisense compound may be formulated in a complexed form, such as an agent having an anionic backbone complexed with cationic lipids or liposomes, which can be taken into cells by an endocytotic mechanism. The analog may be conjugated, e.g., at its 5' or 3' end, to an arginine rich peptide, e.g., the HIV TAT protein, or polyarginine, to facilitate transport into the target host cell.

II. Target Flaviviruses

The present invention is based on the discovery that effective inhibition of flavivirus replication can be achieved by exposing flavivirus-infected cells to oligomeric analogs (i) targeted to the 3'-CS (or 5'-CS) region of flaviviral RNA and (ii) having physical and pharmacokinetic features which allow effective interaction between the analog and the viral RNA within host cells. In one aspect, the analogs can be used in treating a mammalian subject infected with the virus.

The invention targets members of the flavivirus genus of the flaviridae family including the viruses described below. Various physical, morphological, and biological characteristics of the flavivirus genes, and members therein, can be found, for example, in Textbook of Human Virology, R. Belshe, ed., $2^{nd}$ Edition, Mosby, 1991, and in one or more of the references cited above. Some of the key biological, pathological and epidemiological characteristics of each flavivirus member are summarized below.

Flavivirus Replication

Flaviviruses are small, enveloped viruses containing a single, positive-strand, genomic RNA, approximately 10,500 nucleotides in length containing short 5' and 3' non-translated regions (NTRs), a single long open reading frame, a 5' cap, and a nonpolyadenylated 3' terminus. The complete nucleotide sequence of numerous flaviviral genomes, including all four dengue serotypes, yellow fever virus, Japanese encephalitis virus, West Nile virus and tick-borne encephalitis virus have been reported. All flaviviral proteins are derived from a single long polyprotein through precise processing events mediated by host as well as virally encoded proteases. The ten gene products encoded by the single open reading frame are translated as a polyprotein organized in the order, capsid (C), preMembrane (prM, which is processed to Membrane (M) just prior to virion release from the cell), Envelope (E) and the seven non-structural (NS) proteins: NS1, NS2a, NS2b, NS3, NS4a, NS4b and NS5 (Leyssen, De Clercq et al. 2000; Brinton 2002).

Figure 1:
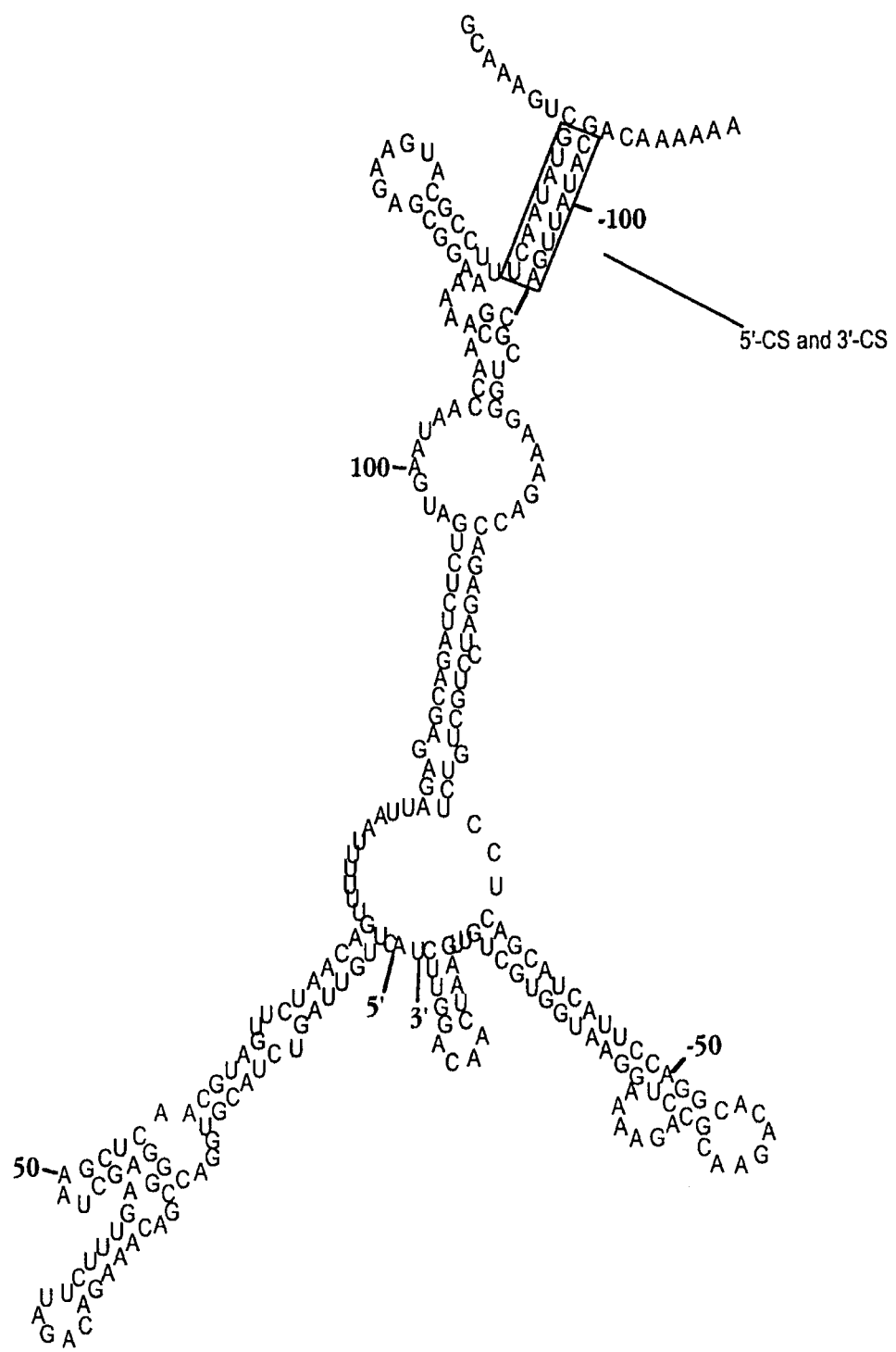
FIG. 1 shows 5'-end (SEQ ID NO:30), 3'-end (SEQ ID NO:31) portion of a flavivirus genome, with secondary structure shown and the 5' and 3' cyclization sequences indicated by a box at the top of the figure.
Figure 2G:
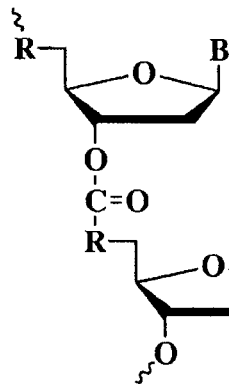
Figure 2G:
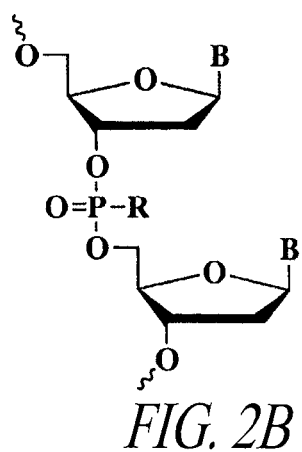
Figure 2G:
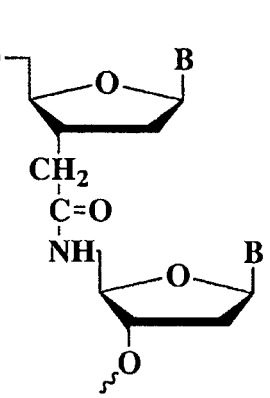
Figure 2G:
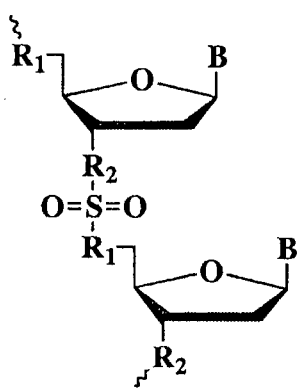
Figure 2G:
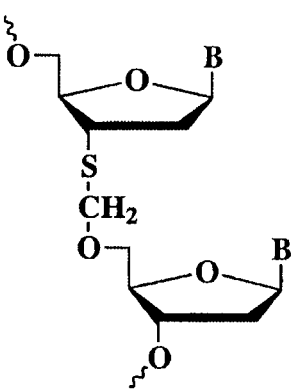
Figure 2G:
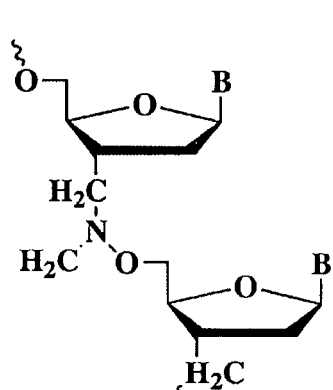
Figure 2G:
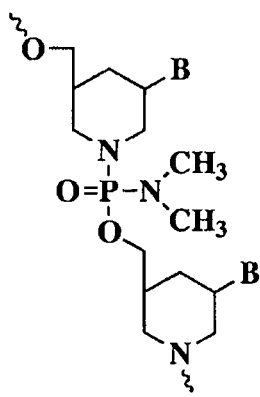

All the mosquito-borne flaviviruses share conserved RNA sequences and structures (Proutski, Gould et al. 1997; Zeng, Falgout et al. 1998; Li, Li et al. 2002). Sequence comparison and RNA secondary structure predictions of flavivirus 3'-NTR and 5'-NTR have revealed several short, well-conserved sequences and indicated that the 3'-terminal region (approximately 90 bases) can be folded in a conserved stem-loop structure (Hahn, Hahn et al. 1987). Conserved stem loop structures have been shown to be important for viral replication in many positive-strand RNA viruses. The flavivirus 3' stem-loop structure primary sequence is not well conserved among flaviviruses but secondary structure is well conserved. A short conserved sequence (3'-CS, SEQ ID NO: 3) has been identified upstream (i.e. in the 5' direction) of the conserved stem-loop structure. Complementarity between the 3'-CS and a conserved sequence at the 5' end of the genome (5'-CS, SEQ ID NO: 1) has been proposed to result in a long-range intramolecular RNA interaction or cyclization of the genomic RNA (Hahn, Hahn et al. 1987; You, Falgout et al. 2001; Corver, Lenches et al. 2003). Recent experiments suggest that base-pairing between these sequences is essential for RNA replication of a Kunjin virus replicon (Khromykh, Meka et al. 2001). A computer-generated predicted secondary-structure between the 5'-CS and 3'-CS of Dengue virus is shown in FIG. 1 (Khromykh, Meka et al. 2001), with the 5'-CS and 3'-CS shown within a box in the upper portion of the figure, and identified herein as SEQ ID NOS: 1 and 3, respectively. Short complementary sequences have also been identified at the 5' and 3' end regions of tick-borne encephalitis viral genomes (SEQ ID NOS: 2 and 4, respectively) and are proposed to function similarly as potential cyclization sequences (Khromykh, Meka et al. 2001).

Dengue Virus

Although flavivirus transmission and the pathology of infection are quite varied among the different viruses, dengue viruses serve as an illustrative example of the genus. Dengue viruses are arthropod-borne viruses (arboviruses) and transmitted to man by mosquitoes of the genus *Aedes*, primarily *A. aegypti* and *A. albopictus*. The viruses cause an illness manifested by high fever, headache, aching muscles and joints, and rash. In some cases, typically in children, a more severe form of infection is seen with dengue hemorrhagic fever/dengue shock syndrome (DHF/DSS), marked by severe hemorrhage, vascular permeability, or both, leading to shock. Individuals who have been infected with a given dengue serotype and are subsequently infected with a different serotype are at significantly greater risk for DHF/DSS. Without diagnosis and prompt medical intervention, the sudden onset and rapid progression of DHF/DSS can be fatal.

Endemic dengue caused by one or more of the four types of dengue viruses is a major public health problem in many tropical and subtropical areas. Sporadic dengue epidemics at times involving over a million individuals continue to occur. Dengue viruses are the most significant group of arthropod-transmitted viruses in terms of global morbidity and mortality with an estimated one hundred million cases of dengue fever occurring annually including 500,000 cases of DHF/DSS. With the global increase in population, urbanization of the population especially throughout the tropics, and the lack of sustained mosquito control measures, the mosquito vectors of dengue have expanded their distribution throughout the tropics, subtropics, and some temperate areas, bringing the risk of dengue infection to over half the world's population. Modern jet travel and human emigration have facilitated global distribution of dengue serotypes such that multiple serotypes of dengue are now endemic in many regions. Accompanying this there has been an increase in the frequency of dengue epidemics and the incidence of DHF/DSS in the last 15 years. For example, in Southeast Asia, DHF/DSS is a leading cause of hospitalization and death among children (Hayes and Gubler 1992).

As described below, many other members of the flavivirus genus are also etiologic agents of severe diseases such as yellow fever, Japanese encephalitis, St. Louis encephalitis, Australian encephalitis, and tick-borne encephalitis.

Yellow Fever Virus

Although an effective vaccine for Yellow Fever has been available for many years, this virus continues to be a leading cause of hemorrhagic fever with mortality rates as high as 50%. Worldwide, there are 200,000 estimated cases of yellow fever (with 30,000 deaths) annually. Small numbers of imported cases also occur in countries free of yellow fever (WHO, Fact Sheet 100, 2001).

Japanese Encephalitis Virus

This arbovirus is the leading cause of viral encephalitis worldwide. Approximately 50,000 cases occur annually in Asia and result in high (30%) mortality or in permanent neurological sequelae (30%) of patients who survive. Epidemic outbreaks caused by JEV continue to pose serious public health problems in the densely populated regions of tropical and subtropical Asia. Transmitted by species of the *Culex* genus of mosquitoes, the disease is clinically manifested as encephalitis, often severe and with a high mortality rate among young children and elderly people. JEV also infects domestic animals such as swine and horses. During the last two decades, immunization using an inactivated JEV vaccine has brought the disease under control in Japan, Korea and Taiwan. However, because of the high cost of manufacturing the vaccine, it is not readily available to those countries where it is needed the most (CDC, Japanese Encephalitis Fact Sheet, 2001).

Murray Valley Encephalitis Virus and Kunjin Virus

These viruses are the causative agents for "Australian encephalitis", a clinical syndrome characterized by aseptic meningitis and/or encephalitis. Both are arboviruses, transmitted by the *Culex* mosquito, and are endemic in Northern Australia. Murray Valley encephalitis symptoms almost invariably include a sudden onset of fever; anorexia and headache. Brain dysfunction may be experienced after a few days and both coma and death may ensue. It is rare for recovery from the encephalitic syndrome to occur without some residual mental or functional disability. Kunjin virus, a virus closely related to West Nile virus (Scherret, Poidinger et al.

2001), causes a clinically similar illness to Murray Valley encephalitis virus but is generally less severe and human infections are reported less frequently.

West Nile Virus

West Nile virus (WNV), another arthropod-borne flavivirus, has emerged in recent years as a deadly health threat to not only humans, but also to other animal species such as horses and birds. In 1999, New York was the first area in North American to report cases of West Nile virus infections. West Nile virus infection in humans has been found previously only in Africa, the Middle East and Eastern Europe. The virus is transmitted to humans and several animal species by mosquitoes which acquire the virus by feeding on infected birds. West Nile virus remains a continued threat to public health. Epidemiologic and virologic studies indicate that live virus persists in mosquito and bird populations. Mosquito control measures were implemented in New York, New Jersey and Connecticut, and many other Eastern states, yet new cases of West Nile virus are being diagnosed. Currently, West Nile virus has been found in nearly every state in the U.S. (Enserink 2002).

Among West Nile virus infected humans, approximately one in every 150 to 300 become ill with fever, myalgia and possible rash. Among those who are symptomatic, approximately 10-15% will have evidence of meningitis (headache, stiff neck) or encephalitis (change of mental status, peripheral neurologic abnormalities, muscle weakness). Almost all fatalities have occurred among humans over the age of 50. The fatality rate among patients with central nervous system infection is between 5% and 11%. Fatalities have been due to prolonged central nervous system dysfunction requiring ventilatory support and leading to secondary complications. Prolonged neurologic symptoms have occurred in survivors of West Nile virus-caused encephalitis.

St. Louis Encephalitis Virus

Although there have been no recent epidemics of St. Louis Encephalitis virus, it remains endemic in the western United States and is the cause of severe disease including asceptic meningitis and/or encephalitis. Another arbovirus, SLEV is responsible for unpredictable and intermittent epidemics with the largest recent U.S. outbreaks occurring in 1975 and 1990. Tick-Borne Encephalitis Tick-borne encephalitis (TBE) is one of the most dangerous human infections occurring in Europe and many parts of Asia. The etiological agent is Tick-borne encephalitis virus (TBEV). TBEV is believed to cause at least 11,000 human cases of encephalitis in Russia, including 89-166 deaths, and about 3000 cases in the rest of Europe annually (Ternovoi, Kurzhukov et al. 2003). TBE viruses are often virulent with symptoms ranging from mild or asymptomatic to severe encephalitis with a mortality rate that approaches 40%. Related viruses within the same group, Louping ill virus (LIV) and Powassan virus (POW), also cause human encephalitis but rarely on an epidemic scale. Two other viruses within the same group, Kyasanur Forest disease virus (KFD) and Alkhurma virus (ALK), are closely related to the TBE complex viruses and tend to cause fatal hemorrhagic fevers rather than encephalitis (Gritsun, Lashkevich et al. 2003).

III. Viral Target Regions and Targeting Sequences

The preferred target sequences are those adjacent and including at least a portion, e.g., at least 2-8 bases, of the 5'-CS or 3'-CS sequences of the positive strand flaviviral RNA. As discussed above, these conserved cyclization sequences (CS) appear to play a role in viral replication by bringing into close proximity the 3' and 5' regions of the viral RNA in order to initiate RNA replication (Hahn, Hahn et al. 1987; Khromykh, Meka et al. 2001). A variety of flaviviral genome sequences are available from well known sources, such as the NCBI GenBank databases. Alternatively, a person skilled in the art can find sequences for many of the subject viruses in the open literature, e.g., by searching for references that disclose sequence information on designated viruses. Once a complete or partial viral sequence is obtained, the 5' and 3' CS sequences of the virus are identified.

GenBank references for exemplary viral nucleic acid sequences containing the 5'-CS and 3'-CS end terminal sequences in the corresponding viral genomes are listed in Table 1 below. It will be appreciated that these sequences are only illustrative of other sequences in the flavirus genus, as may be available from available gene-sequence databases of literature or patent resources. The sequences below, identified as SEQ ID NOS: 5-15, are also listed in Table 3 at the end of the specification. The conserved 5'-CS and 3'-CS are shown in bold in Table 1 and listed as SEQ ID NOS: 1-4 in Table 1.

Another group of exemplary target sequences are the complements of SEQ ID NOS: 5-15; that is the sequences that have the complementary anti-parallel sequence of one of identified sequences 5-15. As an example, the complement of SEQ ID NO: 5 (5'GUCAAUAUGCUAAAACGCGG-3') is 5'-CCGCGUUUUAGCAUAUUGAC-3 (SEQ ID NO:28).

TABLE 1

Exemplary 5'-CS and 3'-CS Target Sequences

| Virus | GenBank Acc. No. | 5'-CS Target Ncts. | SEQ ID NO. | Target Sequence (5' to 3') |
|---|---|---|---|---|
| St. Louis encephalitis | M16614 | 138-157 | 5 | GUCAAUAUGCUA AAACGCGG |
| Murray Valley encephalitis | AF161266 | 135-154 | | |
| West Nile | M12294 | 136-155 | | |
| Kunjin | D00246 | 115-134 | | |
| Japanese encephalitis | M18370 | 135-154 | 6 | AUCAAUAUGCUG AAACGCGG |
| Yellow fever | X03700 | 155-174 | 7 | GUCAAUAUGGUA CGACGAGG |
| Dengue-Type 1 | M87512 | 115-135 | 8 | CUUUCAAUAUGC UGAAACGCG |
| Dengue-Type 2 | M19197 | 131-151 | | |
| Dengue-Type 4 | M14931 | 133-153 | | |

TABLE 1-continued Exemplary 5'-CS and 3'-CS Target Sequences

| Virus | GenBank Acc. No. | 5'-CS Target Ncts. | SEQ ID NO. | Target Sequence (5' to 3') |
|---|---|---|---|---|
| Dengue-Type 3 | M93130 | 129-149 | 9 | CUAUCAAUAUGCUGAAACGCG |
| Tick borne encephalitis | U27495 | 108-129 | 10 | CAGCUUAGGAGA<br>ACAAGAGCUG |
| Powassen | L06436 | 81-102 | | |
| Louping III | Y07863 | 105-126 | | |
| Kyasanur Forest disease | X74111 | 94-115 | | |
| Alkhurma | AF331718 | 90-111 | | |
| West Nile | M12294 | 132-151 | 11 | GGCUGUCAAUAU<br>GCUAAAAC |
| St. Louis encephalitis | M18370 | 10861-10882 | 12 | AACAGCAUAUUG<br>ACACCUGGGA |
| Japanese encephalitis | | | | |
| Murray Valley encephalitis | AF161266 | 10899-10920 | | |
| West Nile | M12294 | 10853-10874 | | |
| Kunjin | AY274505 | 10914-10934 | | |
| Yellow fever | X03700 | 10745-10767 | 13 | UGGGACCAUAUU<br>GACGCCAGGGA |
| Dengue-Type 1 | M87512 | 10609-10630 | 14 | AAACAGCAUAUU<br>GACGCUGGGA |
| Dengue-Type 2 | M19197 | 10595-10616 | | |
| Dengue-Type 3 | M93130 | 10588-10609 | | |
| Dengue-Type 4 | M14931 | 10540-10561 | | |
| Tick borne encephalitis | U27495 | 11057-11078 | 15 | CGGUUCUUGUUC<br>UCCCUGAGCC |
| Powassen | L06436 | 10755-10776 | | |
| Louping III | Y07863 | 10787-10808 | | |

The degree of complementarity between the target and targeting sequence is sufficient to form a stable duplex. The region of complementarity of the antisense oligomers with the target RNA sequence may be as short as 8-11 bases, but is preferably 12-15 bases or more, e.g. 12-20 bases, or 12-25 bases. An antisense oligomer of about 15 bases is generally long enough to have a unique complementary sequence in the viral genome. In addition, a minimum length of complementary bases may be required to achieve the requisite binding $T_m$, as discussed below.

Oligomers as long as 40 bases may be suitable, where at least the minimum number of bases, e.g., 8-11, preferably 12-15 bases, are complementary to the target sequence. In general, however, facilitated or active uptake in cells is optimized at oligomer lengths less than about 30, preferably less than 25, and more preferably 20 or fewer bases. For PMO oligomers, described further below, an optimum balance of binding stability and uptake generally occurs at lengths of 13-23 bases.

The oligomer may be 100% complementary to the viral nucleic acid target sequence, or it may include mismatches, e.g., to accommodate variants, as long as a heteroduplex formed between the oligomer and viral nucleic acid target sequence is sufficiently stable to withstand the action of cellular nucleases and other modes of degradation which may occur in vivo. Oligomer backbones which are less susceptible to cleavage by nucleases are discussed below. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the viral nucleic acid target sequence, it is effective to stably and specifically bind to the target sequence, such that a biological activity of the nucleic acid target, e.g. cyclization of the viral RNA, is modulated.

The stability of the duplex formed between the oligomer and the target sequence is a function of the binding $T_m$ and the susceptibility of the duplex to cellular enzymatic cleavage. The $T_m$ of an antisense compound with respect to complementary-sequence RNA may be measured by conventional methods, such as those described by Hames et al., Nucleic Acid Hybridization, IRL Press, 1985, pp. 107-108. Each antisense oligomer should have a binding $T_m$, with respect to a complementary-sequence RNA, of greater than body temperature and preferably greater than 45° C. $T_m$'s in the range 60-80° C. or greater are preferred. According to well known principles, the $T_m$ of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high $T_m$ (50° C. or greater) at a length of 15 bases or less are generally preferred over those requiring 20+ bases for high $T_m$ values.

Table 2 below lists exemplary targeting sequences directed against the 5'-CS and 3'-CS for selected viruses of the flavivirus genus. These sequences, identified by SEQ ID NOS:16-27, are complementary and antiparallel to the sequences identified as SEQ ID NOS:5-15 above (SEQ ID NO:19 is complementary to SEQ ID NO:8, and complementary with one mismatch to SEQ ID NO:9, SEQ ID NO:27 is targeted to a Dengue Type 2 virus 3'-cyclization sequence). As noted above, the actual target sequence in the oligonucleotide analog may be complementary to only a portion of the corresponding target sequence in Table 1, including a portion of the sequence in SEQ ID NO:1 or its complement SEQ ID NO:3, or SEQ ID NO:2 or its complement SEQ ID NO:4.

More generally, the invention contemplates, as exemplary targeting sequences, a sequence of at least 8 bases complementary to a region of the virus' positive strand RNA genome that includes at least a portion of the genome's 5' or 3' cyclization sequence SEQ ID NO:1 or its complement SEQ ID NO:3 for the group of flavivirus identified with this 5'-CS, or SEQ ID NO:2 or its complement SEQ ID NO:4 for the group of flavivirus identified with this 5'-CS. In a preferred embodiment, the targeting sequence is complementary to at least a portion of the genome's 3' cyclization sequence identified as SEQ ID NO:3 for one group of flaviviruses, and as SEQ ID NO: 4 for another group of flaviviruses. The targeting sequence contains a sufficient number of bases in the CS sequence to disrupt base pairing between the virus' 5' and 3' cyclization sequences, that is disrupt the paired-base stem secondary structure shown in the cyclization box as illustrated in FIG. 1. The number of targeting sequences needed to disrupt this structure is preferably at least 2-4 bases complementary to one of the two complementary cyclization sequences, plus bases complementary to adjacent target-sequence bases.

In one embodiment, the targeting sequence includes bases complementary to the entire 5' or 3' cyclization sequence of the selected virus, i.e., any of SEQ ID NOS:1-4.

In another embodiment, the targeting sequence is complementary to corresponding complementary regions of the two cyclization sequences. As an example, an 8-base target sequence containing complementary 4-base portions of the two cyclization sequences shown at the top of the sequence box in FIG. 1 has the discontinuous sequence 5'CAUA . . . UAUG3'. A targeting sequence effective to bind to and disrupt this sequence would have the sequence 5'CATA . . . TATG3', where " . . . " could be a direct 5'-3' subunit link, or a spacer, as a PEG linker, designed to accommodate the discontinuity in the target sequence.

The latter embodiment represents a specific case of an antisense oligonucleotide analog, in accordance with another aspect of the invention, that is directed to complementary portions of sequences forming a "stem" secondary structure in RNA, and includes as targeting bases, bases complementary to both strands of the stem structure, for purposes of disrupting the stem structure.

TABLE 2

Exemplary Targeting Sequences Against the 5'-CS and 3'-CS of Flaviviruses

| Virus | GenBank Acc. No. | 5'-CS Targeting Sequences (5' to 3') | SEQ ID NO. |
|---|---|---|---|
| St. Louis encephalitis | M16614 | CCGCGTTTTAGCATATTGAC | 16 |
| Murray Valley encephalitis | AF161266 | | |
| West Nile | M12294 | | |
| Kunjin | D00246 | | |
| | | | |
| Japanese encephalitis | M18370 | CCGCGTTTCAGCATATTGAT | 17 |
| | | | |
| Yellow fever | X03700 | CCTCGTCGTACCATATTGAC | 18 |
| | | | |
| Dengue-Type 1 | M87512 | CGCGTTTCAGCATATTGAAAG | 19 |
| Dengue-Type 2 | M19197 | | |
| Dengue-Type 3 | M93130 | | |
| Dengue-Type 4 | M14931 | | |
| | | | |
| Tick borne encephalitis | U27495 | CAGCTCTTGTTCTCCTAAGCTG | 20 |
| Powassen | L06436 | | |
| Louping III | Y07863 | | |
| Kyasanu Forest disease | X74111 | | |
| Alkhurma | AF331718 | | |
| | | | |
| West Nile | M12294 | GTTTTAGCATATTGACAGCC | 21 |

| Virus | GenBank Acc. No. | 3'-CS Targeting Sequences (5' to 3') | SEQ ID NO. |
|---|---|---|---|
| St. Louis encephalitis | | TCCCAGGTGTCAATATGCTGTT | 22 |
| Japanese encephalitis | M18370 | | |
| Murray Valley encephalitis | AF161266 | | |
| West Nile | M12294 | | |
| Kunjin | AY274505 | | |
| | | | |
| Yellow fever | X03700 | TCCCTGGCGTCAATATGGTCCCA | 23 |
| | | | |
| Dengue-Type 1 | M87512 | TCCCAGCGTCAATATGCTGTTT | 24 |
| Dengue-Type 2 | M19197 | | |
| Dengue-Type 3 | M93130 | | |
| Dengue-Type 4 | M14931 | | |

TABLE 2-continued

Exemplary Targeting Sequences Against the 5'-CS and 3'-CS of Flaviviruses

| | | | |
|---|---|---|---|
| Tick borne encephalitis | U27495 | GGCTCAGGGAGAACAAGAACCG | 25 |
| Powassen | L06436 | | |
| Louping III | Y07863 | | |
| West Nile | M12294 | CAGGTGTCAATATGCTGTTTTG | 26 |
| Dengue-Type 2 | M19197 | CCCAGCGTCAATATGCTG | 27 |

Note that the target sequence in Table 1 is indicated as containing uracil (U) bases characteristic of RNA, and the targeting sequences in Table 2, as containing thymine bases characteristic of DNA. It will be understood that the targeting sequence bases may be normal DNA bases or analogs thereof, e.g., uracil, that are capable of Watson-Crick base pairing to target-sequence RNA bases.

IV. Antisense Oligomers

A. Properties

As detailed above, the antisense oligomer has a base sequence directed to a targeted portion of the viral genome, preferably either the 5'-CS or 3'-CS. In addition, the oligomer is able to effectively target infecting viruses, when administered to an infected host cell, e.g. in an infected animal subject. This requirement is met when the oligomer compound (a) has the ability to be actively taken up by mammalian cells, and (b) once taken up, form a duplex with the target ssRNA with a $T_m$ greater than about 50° C.

As will be described below, the ability to be taken up by cells requires that the oligomer backbone be substantially uncharged, and, preferably, that the oligomer structure is recognized as a substrate for active or facilitated transport across the cell membrane. The ability of the oligomer to form a stable duplex with the target RNA will also depend on the oligomer backbone, as well as factors noted above, the length and degree of complementarity of the antisense oligomer with respect to the target, the ratio of G:C to A:T base matches, and the positions of any mismatched bases. The ability of the antisense oligomer to resist cellular nucleases promotes survival and ultimate delivery of the agent to the cell cytoplasm.

Below are disclosed methods for testing any given, substantially uncharged backbone for its ability to meet these requirements.

A1. Active or Facilitated Uptake by Cells

The antisense compound may be taken up by host cells by facilitated or active transport across the host cell membrane if administered in free (non-complexed) form, or by an endocytotic mechanism if administered in complexed form.

In the case where the agent is administered in free form, the antisense compound should be substantially uncharged, meaning that a majority of its intersubunit linkages are uncharged at physiological pH. Experiments carried out in support of the invention indicate that a small number of net charges, e.g., 1-2 for a 15- to 20-mer oligomer, can in fact enhance cellular uptake of certain oligomers with substantially uncharged backbones. The charges may be carried on the oligomer itself, e.g., in the backbone linkages, or may be terminal charged-group appendages. Preferably, the number of charged linkages is no more than one charged linkage per four uncharged linkages. More preferably, the number is no more than one charged linkage per ten, or no more than one per twenty, uncharged linkages. In one embodiment, the oligomer is fully uncharged.

An oligomer may also contain both negatively and positively charged backbone linkages, as long as opposing charges are present in approximately equal number. Preferably, the oligomer does not include runs of more than 3-5 consecutive subunits of either charge. For example, the oligomer may have a given number of anionic linkages, e.g. phosphorothioate or N3'→P5' phosphoramidate linkages, and a comparable number of cationic linkages, such as N,N-diethylenediamine phosphoramidates (Dagle, Littig et al. 2000). The net charge is preferably neutral or at most 1-2 net charges per oligomer.

In addition to being substantially or fully uncharged, the antisense agent is preferably a substrate for a membrane transporter system (i.e., a membrane protein or proteins) capable of facilitating transport or actively transporting the oligomer across the cell membrane. This feature may be determined by one of a number of tests for oligomer interaction or cell uptake, as follows.

A first test assesses binding at cell surface receptors, by examining the ability of an oligomer compound to displace or be displaced by a selected charged oligomer, e.g., a phosphorothioate oligomer, on a cell surface. The cells are incubated with a given quantity of test oligomer, which is typically fluorescently labeled, at a final oligomer concentration of between about 10-300 nM. Shortly thereafter, e.g., 10-30 minutes (before significant internalization of the test oligomer can occur), the displacing compound is added, in incrementally increasing concentrations. If the test compound is able to bind to a cell surface receptor, the displacing compound will be observed to displace the test compound. If the displacing compound is shown to produce 50% displacement at a concentration of 10× the test compound concentration or less, the test compound is considered to bind at the same recognition site for the cell transport system as the displacing compound.

A second test measures cell transport, by examining the ability of the test compound to transport a labeled reporter, e.g., a fluorescence reporter, into cells. The cells are incubated in the presence of labeled test compound, added at a final concentration between about 10-300 nM. After incubation for 30-120 minutes, the cells are examined, e.g., by microscopy, for intracellular label. The presence of significant intracellular label is evidence that the test compound is transported by facilitated or active transport.

The antisense compound may also be administered in complexed form, where the complexing agent is typically a polymer, e.g., a cationic lipid, polypeptide, or non-biological cationic polymer, having an opposite charge to any net charge on the antisense compound. Methods of forming complexes, including bilayer complexes, between anionic oligonucleotides and cationic lipid or other polymer components, are well known. For example, the liposomal composition Lipofectin® (Feigner, Gadek et al. 1987), containing the cationic lipid DOTMA (N-[1-(2,3-dioleyloxy)propyl]-N,N,N-trimethylammonium chloride) and the neutral phospholipid DOPE (dioleyl phosphatidyl ethanolamine), is widely used. After administration, the complex is taken up by cells through an endocytotic mechanism, typically involving particle encapsulation in endosomal bodies.

The antisense compound may also be administered in conjugated form with an arginine-rich peptide linked to the 5' or 3' end of the antisense oligomer. The peptide is typically 8-16 amino acids and consists of a mixture of arginine, and other amino acids including phenyalanine and cysteine. Exposure of cells to the peptide conjugated oligomer results in enhanced intracellular uptake and delivery to the RNA target (Moulton, Nelson et al. 2004).

Alternatively, and according to another aspect of the invention, the requisite properties of oligomers with any given backbone can be confirmed by a simple in vivo test, in which a labeled compound is administered to an animal, and a body fluid sample, taken from the animal several hours after the oligomer is administered, assayed for the presence of heteroduplex with target RNA. This method is detailed in subsection D below.

A2. Substantial Resistance to RNaseH

Two general mechanisms have been proposed to account for inhibition of expression by antisense oligonucleotides (Agrawal, Mayrand et al. 1990; Bonham, Brown et al. 1995; Boudvillain, Guerin et al. 1997). In the first, a heteroduplex formed between the oligonucleotide and the viral RNA acts as a substrate for RNaseH, leading to cleavage of the viral RNA. Oligonucleotides belonging, or proposed to belong, to this class include phosphorothioates, phosphotriesters, and phosphodiesters (unmodified "natural" oligonucleotides). Such compounds expose the viral RNA in an oligomer:RNA duplex structure to hydrolysis by RNaseH, and therefore loss of function.

A second class of oligonucleotide analogs, termed "steric blockers" or, alternatively, "RNaseH inactive" or "RNaseH resistant", have not been observed to act as a substrate for RNaseH, and are believed to act by sterically blocking target RNA nucleocytoplasmic transport, splicing, translation, or replication. This class includes methylphosphonates (Toulme, Tinevez et al. 1996), morpholino oligonucleotides, peptide nucleic acids (PNA's), certain 2'-O-allyl or 2'-O-alkyl modified oligonucleotides (Bonham, Brown et al. 1995), and N3'→P5' phosphoramidates (Ding, Grayaznov et al. 1996; Gee, Robbins et al. 1998).

A test oligomer can be assayed for its RNaseH resistance by forming an RNA:oligomer duplex with the test compound, then incubating the duplex with RNaseH under standard assay conditions, as described in Stein et al. After exposure to RNaseH, the presence or absence of intact duplex can be monitored by gel electrophoresis or mass spectrometry.

A3. In Vivo Uptake

In accordance with another aspect of the invention, there is provided a simple, rapid test for confirming that a given antisense oligomer type provides the required characteristics noted above, namely, high $T_m$, ability to be actively taken up by the host cells, and substantial resistance to RNaseH. This method is based on the discovery that a properly designed antisense compound will form a stable heteroduplex with the complementary portion of the viral RNA target when administered to a mammalian subject, and the heteroduplex subsequently appears in the urine (or other body fluid). Details of this method are also given in co-owned U.S. patent application Ser. No. 09/736,920, entitled "Non-Invasive Method for Detecting Target RNA" (Non-Invasive Method), the disclosure of which is incorporated herein by reference.

Briefly, a test oligomer containing a backbone to be evaluated, having a base sequence targeted against a known RNA, is injected into an animal, e.g., mammalian subject. The antisense oligomer may be directed against any intracellular RNA, including a host RNA or the RNA of an infecting virus. Several hours (typically 8-72) after administration, the urine is assayed for the presence of the antisense-RNA heteroduplex. If heteroduplex is detected, the backbone is suitable for use in the antisense oligomers of the present invention.

The test oligomer may be labeled, e.g. by a fluorescent or a radioactive tag, to facilitate subsequent analyses, if it is appropriate for the mammalian subject. The assay can be in any suitable solid-phase or fluid format. Generally, a solid-phase assay involves first binding the heteroduplex analyte to a solid-phase support, e.g., particles or a polymer or test-strip substrate, and detecting the presence/amount of heteroduplex bound. In a fluid-phase assay, the analyte sample is typically pretreated to remove interfering sample components. If the oligomer is labeled, the presence of the heteroduplex is confirmed by detecting the label tags. For non-labeled compounds, the heteroduplex may be detected by immunoassay if in solid phase format or by mass spectroscopy or other known methods if in solution or suspension format.

When the antisense oligomer is complementary to a virus-specific region of the viral genome (such as the region encompassing the flavivirus 5'-CS and 3'-CS), the method can be used to detect the presence of a given ssRNA virus. The method can also be used to monitor the reduction in the amount of virus during a treatment method.

B. Exemplary Oligomer Backbones

Examples of nonionic linkages that may be used in oligonucleotide analogs are shown in FIGS. 2A-2G. In these figures, B represents a purine or pyrimidine base-pairing moiety effective to bind, by base-specific hydrogen bonding, to a base in a polynucleotide, preferably selected from adenine, cytosine, guanine and uracil. Suitable backbone structures include carbonate (2A, R=O) and carbamate (2A, R=NH$_2$) linkages (Mertes and Coats 1969; Gait, Jones et al. 1974); alkyl phosphonate and phosphotriester linkages (2B, R=alkyl or —O-alkyl) (Lesnikowski, Jaworska et al. 1990); amide linkages (2C) (Blommers, Pieles et al. 1994); sulfone and sulfonamide linkages (2D, R$_1$, R$_2$=CH$_2$) (Roughten, 1995; McElroy, 1994); and a thioformacetyl linkage (2E) (Matteucci, 1990; Cross, 1997). The latter is reported to have enhanced duplex and triplex stability with respect to phosphorothioate antisense compounds (Cross, 1997). Also reported are the 3'-methylene-N-methylhydroxyamino compounds of structure 2F (Mohan, 1995).

Peptide nucleic acids (PNAs) (FIG. 2G) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm et al., 1993). The backbone of PNAs is formed by peptide bonds rather than phosphodiester bonds, making them well-suited for antisense applications. The backbone is uncharged, resulting in PNA/DNA or PNA/RNA duplexes which exhibit greater than normal thermal stability. PNAs are not recognized by nucleases or proteases.

A preferred oligomer structure employs morpholino-based subunits bearing base-pairing moieties, joined by uncharged linkages, as described above. Especially preferred is a substantially uncharged phosphorodiamidate-linked morpholino oligomer, such as illustrated in FIGS. 3A-3D. Morpholino oligonucleotides, including antisense oligomers, are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

Important properties of the morpholino-based subunits include: the ability to be linked in an oligomeric form by stable, uncharged backbone linkages; the ability to support a nucleotide base (e.g. adenine, cytosine, guanine or uracil) such that the polymer formed can hybridize with a complementary-base target nucleic acid, including target RNA, with high $T_m$, even with oligomers as short as 10-14 bases; the ability of the oligomer to be actively transported into mammalian cells; and the ability of the oligomer:RNA heteroduplex to resist RNAse degradation.

Exemplary backbone structures for antisense oligonucleotides of the invention include the β-morpholino subunit types shown in FIGS. 3A-3D, each linked by an uncharged, phosphorus-containing subunit linkage. FIG. 3A shows a phosphorus-containing linkage which forms the five atom repeating-unit backbone, where the morpholino rings are linked by a 1-atom phosphoamide linkage. FIG. 3B shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

Figure 3C:
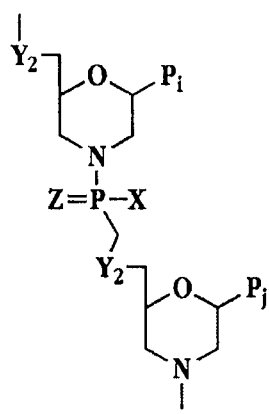
Figure 3D:
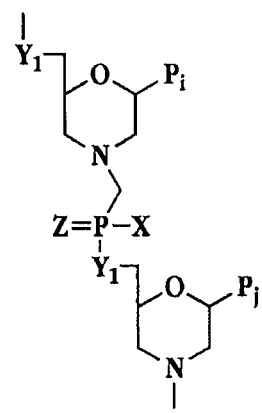

The linkages shown in FIGS. 3C and 3D are designed for 7-atom unit-length backbones. In Structure 3C, the X moiety is as in Structure 3B, and the moiety Y may be methylene, sulfur, or, preferably, oxygen. In Structure 3D, the X and Y moieties are as in Structure 3B. Particularly preferred morpholino oligonucleotides include those composed of morpholino subunit structures of the form shown in FIG. 3B, where X=$NH_2$ or $N(CH_3)_2$, Y=O, and Z=O.

As noted above, the substantially uncharged oligomer may advantageously include a limited number of charged linkages, e.g. up to about 1 per every 5 uncharged linkages, more preferably up to about 1 per every 10 uncharged linkages. Therefore a small number of charged linkages, e.g. charged phosphoramidate or phosphorothioate, may also be incorporated into the oligomers.

The antisense compounds can be prepared by stepwise solid-phase synthesis, employing methods detailed in the references cited above. In some cases, it may be desirable to add additional chemical moieties to the antisense compound, e.g. to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense oligomer, it is generally of course desirable to select chemical compounds of groups that are biocompatible and likely to be tolerated by a subject without undesirable side effects.

V. Inhibition of Viral Replication

The antisense compounds detailed above are useful in inhibiting replication of flaviviruses in animal cells, including mammalian cells, e.g., human cells, and avian cells. In one embodiment, such inhibition is effective in treating infection of a host animal by these viruses. Accordingly, the method comprises, in one embodiment, contacting a cell infected with the virus with an antisense agent effective to inhibit the replication of the specific virus. In this embodiment, the antisense agent is administered to a mammalian subject, e.g., human or domestic animal, infected with a given virus, in a suitable pharmaceutical carrier. It is contemplated that the antisense oligonucleotide arrests the growth of the RNA virus in the host. The RNA virus may be decreased in number or eliminated with little or no detrimental effect on the normal growth or development of the host.

A. Identification of the Infective Agent

The specific virus causing the infection can be determined by methods known in the art, e.g. serological or cultural methods, or by methods employing the antisense oligomers of the present invention.

Serological identification employs a viral sample or culture isolated from a biological specimen, e.g., stool, urine, cerebrospinal fluid, blood, etc., of the subject. Immunoassay for the detection of virus is generally carried out by methods routinely employed by those of skill in the art, e.g., ELISA or Western blot. In addition, monoclonal antibodies specific to particular viral strains or species are often commercially available.

Culture methods may be used to isolate and identify particular types of virus, by employing techniques including, but not limited to, comparing characteristics such as rates of growth and morphology under various culture conditions.

Another method for identifying the viral infective agent in an infected subject employs one or more antisense oligomers targeting a spectrum of flavivirus species. Sequences targeting any characteristic viral RNA can be used. The desired target sequences are preferably (i) common to broad virus families/genera, and (ii) not found in the infected host, e.g., humans. Characteristic nucleic acid sequences for a large number of infectious viruses are available in public databases, and may serve as the basis for the design of specific oligomers.

For each plurality of oligomers, the following steps are carried out: (a) the oligomer(s) are administered to the subject; (b) at a selected time after said administering, a body fluid sample is obtained from the subject; and (c) the sample is assayed for the presence of a nuclease-resistant heteroduplex comprising the antisense oligomer and a complementary portion of the viral genome. Steps (a)-(c) are carried for at least one such oligomer, or as many as is necessary to identify the virus or family of viruses. Oligomers can be administered and assayed sequentially or, more conveniently, concurrently. The virus is identified based on the presence (or absence) of a heteroduplex comprising the antisense oligomer and a complementary portion of the viral genome of the given known virus or family of viruses.

Preferably, a first group of oligomers, targeting broad families, is utilized first, followed by selected oligomers complementary to specific genera and/or species and/or strains within the broad family/genus thereby identified. This second group of oligomers includes targeting sequences directed to specific genera and/or species and/or strains within a broad family/genus. Several different second oligomer collections, i.e. one for each broad virus family/genus tested in the first stage, are generally provided. Sequences are selected which are (i) specific for the individual genus/species/strains being tested and (ii) not found in humans.

B. Administration of the Antisense Oligomer

Effective delivery of the antisense oligomer to the target nucleic acid is an important aspect of treatment. In accordance with the invention, routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. For example, an appropriate route for delivery of an antisense oligomer in the treatment of a viral infection of the skin is topical delivery, while delivery of an antisense oligomer for the treatment of a viral respiratory infection is by inhalation. The oligomer may also be delivered directly to the site of viral infection, or to the bloodstream.

The antisense oligomer may be administered in any convenient vehicle which is physiologically acceptable. Such a composition may include any of a variety of standard pharmaceutically accepted carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

In some instances, liposomes may be employed to facilitate uptake of the antisense oligonucleotide into cells. (See, e.g., Williams, S. A., *Leukemia* 10(12): 1980-1989, 1996; Lappalainen et al., *Antiviral Res.* 23:119, 1994; Uhlmann et al., ANTISENSE OLIGONUCLEOTIDES: A NEW THERAPEUTIC PRINCIPLE, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. The oligonucleotides may also be administered in microspheres or microparticles. (See, e.g., Wu, G. Y. and Wu, C. H., *J. Biol. Chem.* 262:4429-4432, 1987). Alternatively, the use of gas-filled microbubbles complexed with the antisense oligomers can enhance delivery to target tissues, as described in U.S. Pat. No. 6,245,747.

Sustained release compositions may also be used. These may include semipermeable polymeric matrices in the form of shaped articles such as films or microcapsules.

In one aspect of the method, the subject is a human subject, e.g., a patient diagnosed as having a localized or systemic viral infection. The condition of a patient may also dictate prophylactic administration of an antisense oligomer of the invention, e.g. in the case of a patient who (1) is immunocompromised; (2) is a burn victim; (3) has an indwelling catheter; or (4) is about to undergo or has recently undergone surgery. In one preferred embodiment, the oligomer is a phosphorodiamidate morpholino oligomer, contained in a pharmaceutically acceptable carrier, and is delivered orally. In another preferred embodiment, the oligomer is a phosphorodiamidate morpholino oligomer, contained in a pharmaceutically acceptable carrier, and is delivered intravenously (IV).

In another application of the method, the subject is a livestock animal, e.g., a chicken, turkey, pig, cow or goat, etc., and the treatment is either prophylactic or therapeutic. In other applications, the infected animal to be treated may be a zoo or wild animal, e.g., seal, penguin, or hawk, such to one or more flavivirus infections. The invention also includes a livestock and poultry food composition containing a food grain supplemented with a subtherapeutic amount of an antiviral antisense compound of the type described above. Also contemplated is, in a method of feeding livestock and poultry with a food grain supplemented with subtherapeutic levels of an antiviral, an improvement in which the food grain is supplemented with a subtherapeutic amount of an antiviral oligonucleotide composition as described above.

The antisense compound is generally administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-25 mg oligomer per 70 kg. In some cases, doses of greater than 25 mg oligomer/patient may be necessary. For IV administration, preferred doses are from about 0.5 mg to 10 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

C. Monitoring of Treatment

An effective in vivo treatment regimen using the antisense oligonucleotides of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of viral infection under treatment, and corresponding adjustments in the dose or treatment regimen, in order to achieve an optimal therapeutic outcome. Treatment may be monitored, e.g., by general indicators of infection, such as complete blood count (CBC), nucleic acid detection methods, immunodiagnostic tests, viral culture, or detection of heteroduplex.

The efficacy of an in vivo administered antisense oligomer of the invention in inhibiting or eliminating the growth of one or more types of RNA virus may be determined from biological samples (tissue, blood, urine, etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of viral protein production, as determined by standard techniques such as ELISA or Western blotting, or (3) measuring the effect on viral titer, e.g. by the method of Spearman-Karber. (See, for example, Pari, G. S. et al., *Antimicrob. Agents and Chemotherapy* 39(5):1157-1161, 1995; Anderson, K. P. et al., *Antimicrob. Agents and Chemotherapy* 40(9):2004-2011, 1996, Cottral, G. E. (ed.) in: Manual of Standard Methods for Veterinary Microbiology, pp. 60-93, 1978).

A preferred method of monitoring the efficacy of the antisense oligomer treatment is by detection of the antisense-RNA heteroduplex. At selected time(s) after antisense oligomer administration, a body fluid is collected for detecting the presence and/or measuring the level of heteroduplex species in the sample. Typically, the body fluid sample is collected 3-24 hours after administration, preferably about 6-24 hours after administering. As indicated above, the body fluid sample may be urine, saliva, plasma, blood, spinal fluid, or other liquid sample of biological origin, and may include cells or cell fragments suspended therein, or the liquid medium and its solutes. The amount of sample collected is typically in the 0.1 to 10 ml range, preferably about 1 ml or less.

The sample may be treated to remove unwanted components and/or to treat the heteroduplex species in the sample to remove unwanted ssRNA overhang regions, e.g. by treatment with RNase. It is, of course, particularly important to remove overhang where heteroduplex detection relies on size separation, e.g., electrophoresis of mass spectroscopy.

A variety of methods are available for removing unwanted components from the sample. For example, since the heteroduplex has a net negative charge, electrophoretic or ion exchange techniques can be used to separate the heteroduplex from neutral or positively charged material. The sample may also be contacted with a solid support having a surface-bound antibody or other agent specifically able to bind the heteroduplex. After washing the support to remove unbound material, the heteroduplex can be released in substantially purified form for further analysis, e.g., by electrophoresis, mass spectroscopy or immunoassay.

The following examples illustrate, but are in no way intended to limit the invention.

Example 1

Antisense Inhibition of West Nile Virus In Vitro

Two PMO oligomers were evaluated for their activity against West Nile virus in cultured Vero cells. One 20mer PMO oligomer targets the 3'-CS region of West Nile virus (WNV 3' CS, SEQ ID NO: 26), the other 20mer PMO compound was a "nonsense" sequence (5'-AGTCTCGACTTGC-TACCTCA-3') (SEQ ID NO:29) with no significant homology to any human, monkey or WNV genetic sequence (NC-1). Both PMO oligomers were conjugated at the 5' end with a peptide ($R_9F_2C$-5'-PMO) to enhance cellular uptake in vitro. Two separate experiments, a "two point" and an "eight point dose response", were performed by adding each PMO oligomer, along with virus inoculum, to cells suspended in standard mammalian tissue culture media supplemented with 2% fetal-calf serum. After 24 hours the cells were scored for cytopathic effect both visually under a microscope, and quantitatively with a microplate reader using the 'neutral-red dye assay' as described (Morrey, Smee et al. 2002). To those skilled in the art, an effective concentration resulting in 50% reduction in viral titer (EC50) of over 20 micromolar is considered low antiviral activity while an EC50 under 20 micromolar indicates substantial antiviral activity. The tables below summarize these results Two Point Dose Response

| PMO compound name | EC50 |
|---|---|
| WNV 3' CS (SEQ ID 26) | 7 micromolar |
| NC-1 | >20 micromolar |

Eight Point Dose Response

| PMO compound name | EC50 |
|---|---|
| WNV 3' CS (SEQ ID 26) | 10 micromolar |
| Negative PMO | >56 micromolar |

Example 2

Antisense Inhibition of Tick Borne Encephalitis

This example describes a study that was devised to test the antiviral activity of antisense PMO compounds of the present invention against two flaviviruses; Tick Borne Encephalitis virus (TBE) and West Nile virus (WN). Two PMO oligomers were evaluated for antiviral activity; TBE 3'CS, SEQ ID NO:25 and; a scramble control sequence DS-scr (5'-AGTCTCGACTTGCTACCTCA-3') (SEQ ID NO:29). Both PMO oligomers were conjugated at the 5' end with an arginine-rich peptide ($R_9F_2C$-5'-PMO) to enhance cellular uptake as described (U.S. Patent Application 60/466,703 and Moulton, Nelson et al. 2004). The WN virus infection provided a negative control infection as there is no homology between WN and the TBE 3'CS targeting PMO. This control indicates the level of non-specific viral suppression of each of the PMOs. The PMO compounds were prepared to provide a 2 mM stock solution, which were then titrated against a standard dose of virus on tissue culture cells. Cells were infected with a multiplicity of infection (moi) of 1 and the virus yield was assessed in samples of supernatant medium taken at 18 hours post infection.

The two virus strains used in this example:
1) TC 401 West Nile 99-34940-31A (New York strain) Passage 2
2) TC 339 Tick Borne Encephalitis virus (Hypr strain) Passage 49

Four T175 tissue culture flasks (NUNC) of SW 13 cells (human caucasian adrenal cortex adenocarcinoma cell line ECAAC 87031801 grown in RPMI 1640 medium plus 5% FBS) at passage 130 were washed twice with trypsin-EDTA (1×) and incubated for 2-3 minutes at 37° C. The cells were resuspended in 11.5 ml growth medium per flask and pooled. A cell count was performed on the pooled cell suspension and the result was 1.74×10$^6$ cells/ml with 99% viability. Six mls of the cell suspension was used to seed four T175 flasks and 40 ml of the cell suspension was diluted to 270 ml. This was dispensed in 3 ml aliquots per well in 15 six-well plates. The plates were incubated overnight to form confluent cell monolayers.

Each of the PMO compounds was diluted to 25, 20, 15, 10 and 5 µM in 4 ml serum-free RPMI 1640 medium. The medium was removed from the wells of two six-well plates. 2 ml of the appropriate compound dilution was dispensed in all wells of a plate and this was repeated on separate plates for both PMO compounds. The plates were incubated at 37° C. for 5 hours. The two viruses were removed from the −70° C. freezer and thawed rapidly. Each virus was diluted to 2×10$^6$ pfu/ml to produce 42 ml serum-free medium. The six-well plates were removed from the incubator and the pre-treatment medium aspirated from all the wells. 1 ml of medium was added to each well of the control plate (no compound). Each set of plates received 1 ml/well of either TBE or WN diluted to 2×10$^6$ pfu/ml. The plates were incubated at room temperature for 1 hour and the medium was then removed and replaced with 2 ml RPMI 1640 plus 1% FBS plus the same concentration of test compound as used to pre-treat the cells. The plates were incubated at 37° C. for 18 hours.

To prepare 24 well plates for determining virus titers, eight T175 tissue culture flasks (NUNC) of SW 13 cells at passage 131 were washed twice with trypsin-EDTA (1×) and incubated for 2-3 minutes at 37° C. The cells were resuspended in 11.5 ml growth medium per flask and pooled. A cell count was performed on the pooled cell suspension and the result was $1.7 \times 10^6$ cells/ml with 99% viability. 80 ml of the cell suspension was diluted to 680 ml. These cells were dispensed as 1 ml per well aliquots in eight 24-well plates. The plates were incubated overnight to form confluent monolayers.

At 18 hours post-infection the supernatant media from the PMO-treated, virus-infected six-well plates were harvested from each individual well. Thirty µl of each harvest was placed in a single cup of a 96-well plate with 270 µl serum-free medium. The remainder of the sample was placed in cryotube and stored at −70° C. The medium was removed from the 24-well plates and 250 µl of the titration dilutions were transferred from the 96-well plates to the 24 well plates which were incubated at 37° C. for one hour. One ml agarose overlay medium was added to each well and after allowing the agarose to set at room temperature the plates were incubated at 37° C. for 5 days. After 5 days the plates were removed from the incubator, 1 ml 10% Formol saline was added to each well and the plates were left at room temperature for 3 hours. The plates were washed under running water to remove the agarose medium and left to drain inverted whilst the remaining plates were washed. Each well then received 1 ml of 0.1% Naphthalene black stain and the plates were left for 30 minutes before the stain was removed and the plates washed under running water. They were then left to dry (inverted) for 3 hours. Viral plaques were counted to determine the titer.

Figures 4A, 4B:
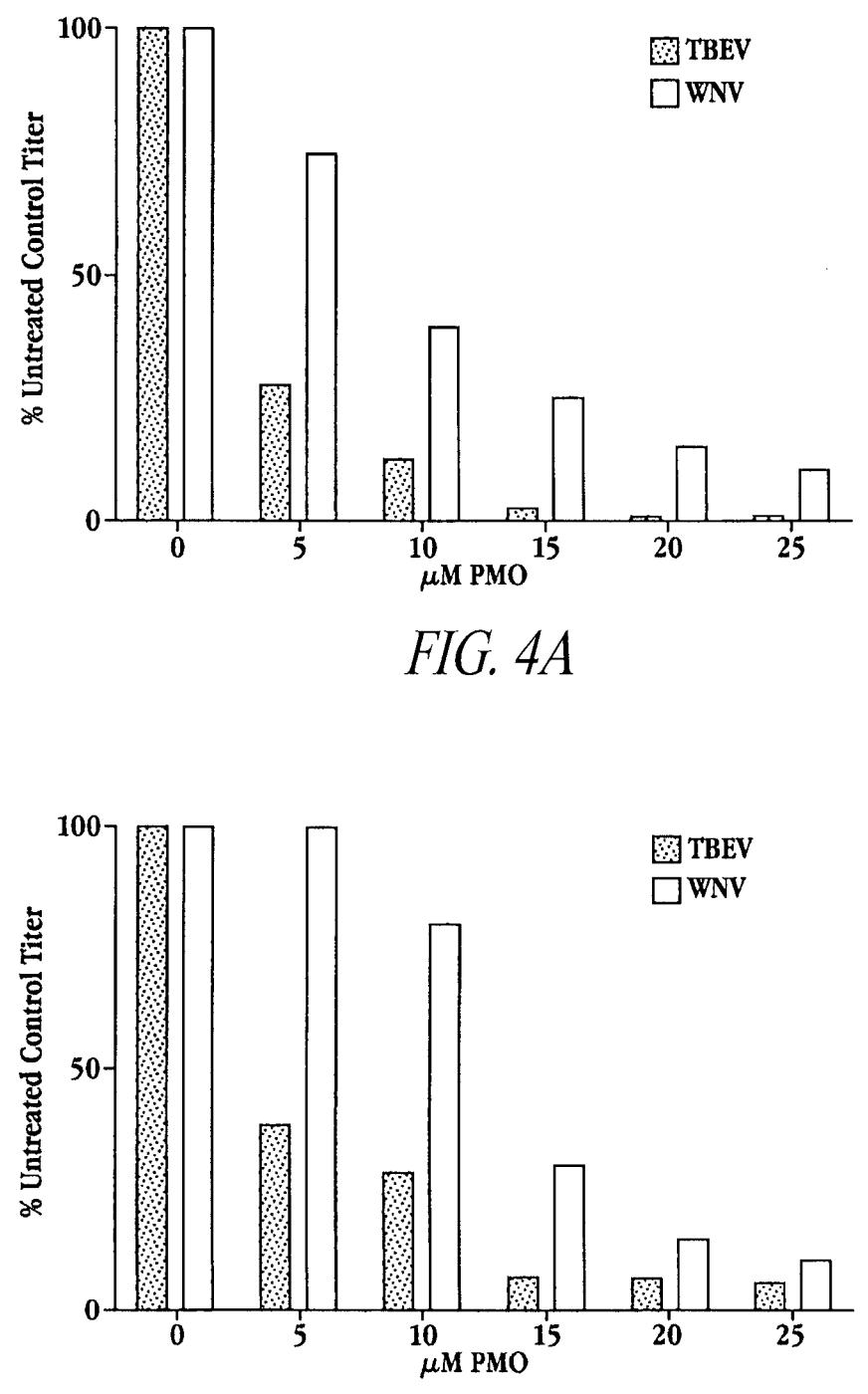

FIGS. 4A and 4B show the viral titer obtained from the PMO-treated infections as % of untreated control, with virus-infected cells infected with either TBEV or WNV and treated with either the TBE antisense compound (FIG. 4A, where the compound has SEQ ID NO:25) or control compound (FIG. 4B, scrambled sequence). As seen from a comparison of the viral titers in FIGS. 24A and 24B, there is a reduction in viral titre in all cells (treated and control) with increasing concentrations of compound, thought to be due to a cell-toxicity effect of the attached arginine-rich peptide present in both antisense and control compounds. At a compound concentration of 15 µM and above, there is seen a sequence-specific increase in TBE viral inhibition, both relative to WNV (FIG. 24A), and relative to the scrambled-sequence control (comparing FIGS. 24A and 24B).

Example 3

Inhibition of Dengue Virus Serotypes 1-4 with Antisense PMO

Dengue Fever/Dengue Hemorrhagic Fever (DF/DHF) has become a major global health problem over the past 20 years. Geographic distribution of the dengue virus (DEN), it's mosquito vectors and the disease burden it causes continue to increase. The World Health Organization estimates that there are 50-100 million new infections yearly. DF/DHF is now a leading cause of hospitalization and death among children in southern Asia, and its incidence is sharply rising in the Americas. There is currently no vaccine or effective therapeutic. One requirement of a successful vaccine or therapeutic is that it be effective against all 4 human serotypes of DEN. The purpose of this study was to evaluate the efficacy and specificity of PMO that target the 3'-CS at inhibiting the replication of four serotypes of DEN in Vero cells in culture. The 5 PMO compounds were designed to target sequence elements in the positive-strand DEN2 RNA that have been recognized as important in viral transcription and/or translation (4,5). The PMO in this study were conjugated to an arginine-rich peptide in order to facilitate entry into Vero E6 cells.

Figure 5A:
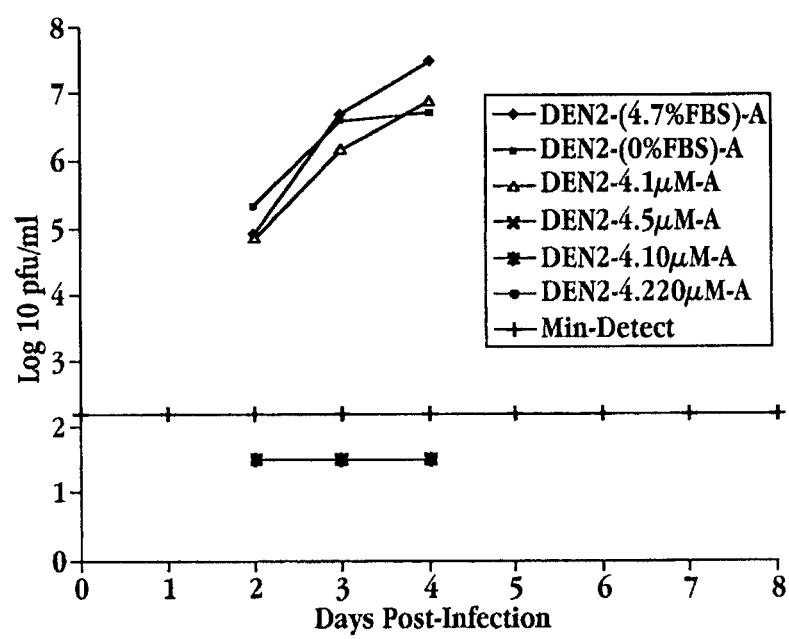
FIGS. 5A-5D are plots of the response of four Dengue virus serotypes to DEN antisense (SEQ ID NO:27).
Figure 5B:
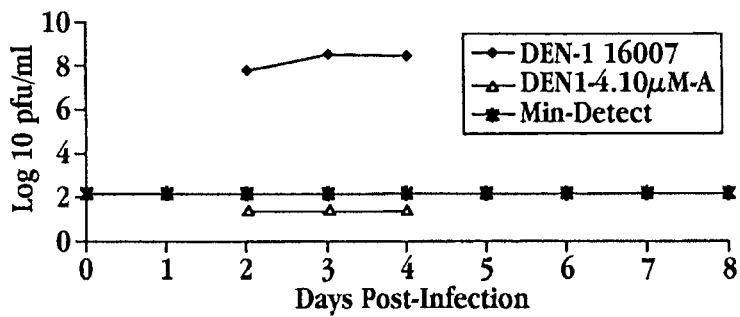
Figure 5C:
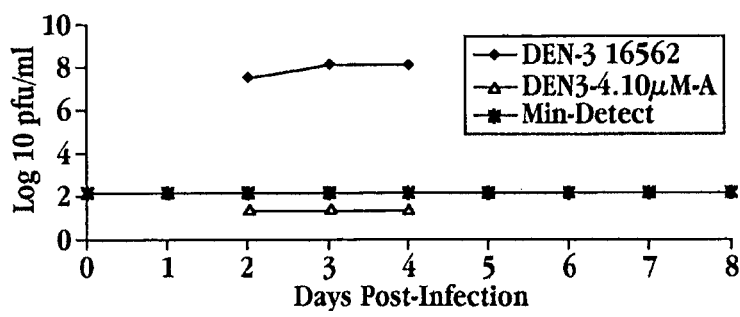
Figure 5D:
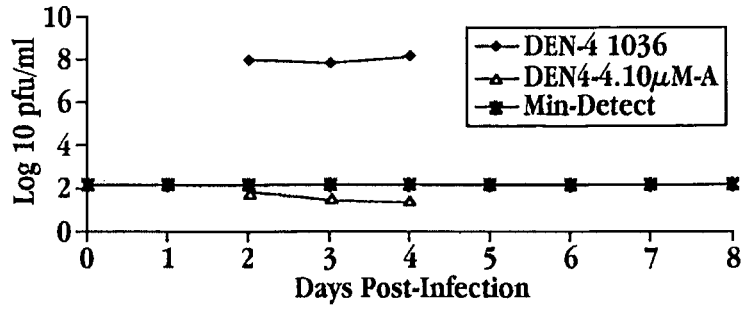

PMOs designed to hybridize to the 3'-CS region of Dengue 2 virus (DEN2), were evaluated for their ability to inhibit Dengue virus replication in mammalian cell culture. The PMO s were conjugated to a short arginine-rich peptide ($R_9F_2C$-5'-PMO) to facilitate their entry into cells in culture. Vero E6 cells were incubated with the PMO agents, inoculated with DEN serotypes 1-4, and viral titer determined by plaque-assay 5-8 days later. The compound targeting 3'-cyclization sequence (3'CS PMO), reduced the titer of DEN2 by over 3 orders of magnitude, compared to controls, in a dose-dependent and sequence-specific manner over a 4-6 day period as shown in FIG. 5A. Ten µM solutions of the 3'-CS PMO each reduced the titer of all four Dengue serotypes by over two orders of magnitude, in some cases below detectable limits as shown in FIGS. 5B-5D. The effective anti-DEN compounds did not alter the titer of West Nile Virus (WNV) grown in Vero E6 cells. These data indicate that the 3'-CS PMO compound is a potential DEN 1-4 therapeutic.

From the foregoing, it will be appreciated how various objects and features of the invention are met. Because the target sequences are conserved across several flaviviruses, a single oligonucleotide analog can be used to treat each of the several viruses. For example, a single analog directed against SEQ ID NO:1 or its complement SEQ ID NO:3 may be used for inhibiting replication of St. Louis encephalitis virus, Murray Valley encephalitis virus, West Nile virus, Kunjin virus, Japanese encephalitis virus, Yellow fever virus, Dengue virus—Types 1, 2, 3, and 4, and West Nile virus, and a single analog directed against SEQ ID NO: 2 or its complement SEQ ID NO: 4 may be used for treating Tick borne encephalitis virus, Powassen virus, Louping III virus, Kyasanur Forest disease virus, and Alkhurma virus.

Where the target sequence is limited to one of the complementary cyclization sequences, the analog would be effective in disrupting the cyclization stem secondary structure in both the genomic sense strand, and the first replication, antisense strand, thereby serving to inhibit viral replication at the level of replication of both the positive and negative strands.

The analog is stable in the body and for some analog structures, e.g., PMO, may be administered orally. Further, the formation of heteroduplexes between the analog and viral target may be used to confirm the presence or absence of infection by a flavivirus, and/or to confirm uptake of the therapeutic agent by the host.

TABLE 3

Sequence Listing Table

| Target Sequences | SEQ ID NO. |
|---|---|
| 5'-UCAAUAUG-3' | 1 |
| 5'-GGAGAACAAGA-3' | 2 |

TABLE 3-continued

Sequence Listing Table

| | SEQ ID NO. |
|---|---|
| 5'-CAUAUUGA-3' | 3 |
| 5'-UCUUGUUCUCC-3' | 4 |
| 5'-GUCAAUAUGCUAAAACGCGG-3' | 5 |
| 5'-AUCAAUAUGCUGAAACGCGG-3 | 6 |
| 5'-GUCAAUAUGGUACGACGAGG-3' | 7 |
| 5'-CUUUCAAUAUGCUGAAACGCG-3' | 8 |
| 5'-CUAUCAAUAUGCUGAAACGCG-3' | 9 |
| 5'-CAGCUUAGGAGAACAAGAGCUG-3' | 10 |
| 5'-AACAGCAUAUUGACACCUGGGA-3' | 12 |
| 5'-UGGGACCAUAUUGACGCCAGGGA-3' | 13 |
| 5-AAACAGCAUAUUGACGCUGGGA-3' | 14 |
| 5'-CGGUUCUUGUUCUCCCUGAGCC-3' | 15 |
| 5'-GGCUGUCAAUAUGCUAAAAC-3' | 11 |

TABLE 3-continued

Sequence Listing Table

| | SEQ ID NO. |
|---|---|
| Oligomer Targeting Sequences | |
| 5'-CCGCGTTTTAGCATATTGAC-3' | 16 |
| 5'-CCGCGTTTCAGCATATTGAT-3' | 17 |
| 5'-CCTCGTCGTACCATATTGAC-3' | 18 |
| 5'-CGCGTTTCAGCATATTGAAAG-3' | 19 |
| 5-CAGCTCTTGTTCTCCTAAGCTG-3' | 20 |
| 5'-GTTTTAGCATATTGACAGCC-3' | 21 |
| 5'-TCCCAGGTGTCAATATGCTGTT-3' | 22 |
| 5'-TCCCTGGCGTCAATATGGTCCCA-3' | 23 |
| 5'-TCCCAGCGTCAATATGCTGTTT-3' | 24 |
| 5'-GGCTCAGGGAGAACAAGAACCG-3' | 25 |
| 5'-CAGGTGTCAATATGCTGTTTTG-3' | 26 |
| 5'-CCCAGCGTCAATATGCTG-3' | 27 |

It is claimed:

1. An in vitro method of inhibiting replication of a Dengue virus in animal cells, comprising contacting the animal cells with a morpholino oligonucleotide consisting of a base sequence set forth in SEQ ID NO:24.

2. The method of claim 1, wherein the morpholino oligonucleotide inhibits replication of Dengue virus Type 1, Dengue virus Type 2, Dengue virus Type 3, Dengue virus Type 4, or any combination thereof.

3. The method of claim 1, wherein the morpholino oligonucleotide is capable of forming a heteroduplex structure with a sequence that includes of a portion of the genome's 5' cyclization sequence identified as SEQ ID NO:1 and a complementary portion of the genome's 3' cyclization sequence identified as SEQ ID NO: 3.

4. The method of claim 1, wherein the morpholino oligonucleotide is a phosphorodiamidate morpholino oligonucleotide.

5. The method of claim 1, wherein the morpholino subunits oligonucleotide comprises phosphorus-containing intersubunit linkages, in accordance with the structure:

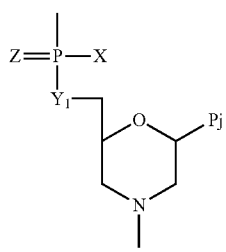

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, amino, alkyl amino, or dialkylamino.

6. A morpholino oligonucleotide consisting of a base sequence set forth in SEQ ID NO:24.

7. The analog morpholino oligonucleotide of claim 6, wherein the morpholino oligonucleotide is capable of forming a heteroduplex structure with a sequence that includes of a portion of a Dengue virus genome's 3' cyclization sequence identified as SEQ ID NO: 3.

8. The morpholino oligonucleotide of claim 6, wherein the morpholino oligonucleotide is a phosphorodiamidate morpholino oligonucleotide.

9. The morpholino oligonucleotide of claim 6, wherein the morpholino oligonucleotide comprises phosphorus-containing intersubunit linkages, in accordance with the structure:

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, amino, alkyl amino, or dialkylamino.

10. The morpholino oligonucleotide of claim 9, wherein X is $NR_2$, wherein R is independently H or a lower alkyl.

11. The morpholino oligonucleotide of claim 10, wherein the lower alkyl is methyl.

12. The morpholino oligonucleotide of claim 11, wherein X is $N(CH_3)_2$.

13. The morpholino oligonucleotide of claim 9, wherein the morpholino oligonucleotide has no more than one charged intersubunit linkage per four uncharged intersubunit linkages.

14. The morpholino oligonucleotide of claim 13, wherein the morpholino oligonucleotide has no more than one charged intersubunit linkage per ten uncharged intersubunit linkages.

15. The morpholino oligonucleotide of claim 6, wherein the morpholino oligonucleotide is conjugated at its 5' or 3' end to an arginine-rich peptide.

16. The morpholino oligonucleotide of claim 15, wherein the morpholino oligonucleotide is conjugated at its 5' end to an arginine-rich peptide.

17. The morpholino oligonucleotide of claim 15, wherein the arginine-rich peptide has 8-16 amino acids.

18. The morpholino oligonucleotide of claim 15, wherein the arginine-rich peptide is $R_9F_2C$.

19. The morpholino oligonucleotide of claim 6, further comprising a polyethylene glycol moiety.

20. A pharmaceutical composition comprising the morpholino oligonucleotide of claim 6 and a pharmaceutically acceptable carrier.

21. The method of claim 5, wherein X is $NR_2$, wherein R is independently H or a lower alkyl.

22. The method of claim 21, wherein the lower alkyl is methyl.

23. The method of claim 22, wherein X is $N(CH_3)_2$.

24. The method of claim 5, wherein the morpholino oligonucleotide has no more than one charged intersubunit linkage per four uncharged intersubunit linkages.

25. The method of claim 24, wherein the morpholino oligonucleotide has no more than one charged intersubunit linkage per ten uncharged intersubunit linkages.

26. The method of claim 1, wherein the morpholino oligonucleotide is conjugated at its 5' or 3' end to an arginine-rich peptide.

27. The method of claim 26, wherein the morpholino oligonucleotide is conjugated at its 5' end to an arginine-rich peptide.

28. The method of claim 26, wherein the arginine-rich peptide has 8-16 amino acids.

29. The method of claim 26, wherein the arginine-rich peptide is $R_9F_2C$.

30. The method of claim 1, wherein the morpholino oligonucleotide further comprises a polyethylene glycol moiety.

* * * * *